United States Patent
Kosari et al.

(10) Patent No.: US 10,203,330 B2
(45) Date of Patent: Feb. 12, 2019

(54) METHODS AND MATERIALS FOR IDENTIFYING AND TREATING MAMMALS HAVING LUNG ADENOCARCINOMA CHARACTERIZED BY NEUROENDOCRINE DIFFERENTIATION

(71) Applicant: Mayo Foundation for Medical Education and Research, Rochester, MN (US)

(72) Inventors: Farhad Kosari, Ellsworth, WI (US); George Vasmatzis, Oronoco, MN (US); Marie-Christine Aubry, Pine Island, MN (US); Cristiane M. Ida, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/456,146

(22) Filed: Mar. 10, 2017

(65) Prior Publication Data

US 2017/0285034 A1 Oct. 5, 2017

Related U.S. Application Data

(63) Continuation of application No. 14/773,488, filed as application No. PCT/US2014/022037 on Mar. 7, 2014, now abandoned.

(60) Provisional application No. 61/775,316, filed on Mar. 8, 2013.

(51) Int. Cl.
| | |
|---|---|
| *C12Q 1/6886* | (2018.01) |
| *G01N 33/574* | (2006.01) |
| *A61K 31/13* | (2006.01) |
| *A61K 31/198* | (2006.01) |
| *A61K 31/225* | (2006.01) |
| *A61K 31/26* | (2006.01) |
| *A61K 31/404* | (2006.01) |
| *A61K 31/428* | (2006.01) |
| *A61K 31/44* | (2006.01) |
| *A61K 31/4439* | (2006.01) |
| *A61K 31/47* | (2006.01) |
| *A61K 31/4709* | (2006.01) |
| *A61K 31/5025* | (2006.01) |
| *A61K 31/506* | (2006.01) |
| *A61K 31/517* | (2006.01) |
| *A61K 31/7135* | (2006.01) |
| *A61K 38/48* | (2006.01) |

(52) U.S. Cl.
CPC ....... *G01N 33/57423* (2013.01); *A61K 31/13* (2013.01); *A61K 31/198* (2013.01); *A61K 31/225* (2013.01); *A61K 31/26* (2013.01); *A61K 31/404* (2013.01); *A61K 31/428* (2013.01); *A61K 31/44* (2013.01); *A61K 31/4439* (2013.01); *A61K 31/47* (2013.01); *A61K 31/4709* (2013.01); *A61K 31/5025* (2013.01); *A61K 31/517* (2013.01); *A61K 31/7135* (2013.01); *A61K 38/482* (2013.01); *C12Q 1/6886* (2013.01); *C12Q 2600/158* (2013.01); *C12Y 304/21* (2013.01); *C12Y 304/21007* (2013.01); *C12Y 304/21068* (2013.01); *G01N 2333/4703* (2013.01); *G01N 2333/71* (2013.01)

(58) Field of Classification Search
CPC ............ C12Q 2600/158; C12Q 1/6886; G01N 2333/4703
See application file for complete search history.

(56) References Cited

U.S. PATENT DOCUMENTS

| | | | |
|---|---|---|---|
| 5,935,787 A | 8/1999 | Sidransky | |
| 7,183,307 B2 | 2/2007 | Hale et al. | |
| 2004/0009489 A1 | 1/2004 | Golub et al. | |
| 2009/0285832 A1 | 11/2009 | The et al. | |
| 2009/0317392 A1 | 12/2009 | Nakamura et al. | |
| 2011/0195072 A1 | 8/2011 | Boulay et al. | |
| 2011/0201598 A1 | 8/2011 | Gujral et al. | |
| 2011/0287034 A1 | 11/2011 | Frank et al. | |

FOREIGN PATENT DOCUMENTS

WO  WO 2013025952  2/2013

OTHER PUBLICATIONS

Arnold et al. Phase II Study of Vandetanib in Small-Cell Lung Cancer Patients After Complete or Partial Response to Induction Chemotherapy With or Without Radiation Therapy: National Cancer Institute of Canada Clinical Trials Group Study; Journal of Clinical Oncology, vol. 25, No. 27, pp. 4278-4284. (Year: 2007).*
Jiang et al. Achaete-Scute Complex Homolog 1 Regulates Tumor-Initiating Capacity in Human Small Cell Lung Cancer; Cancer Research, vol. 69, No. 3, pp. 845-854. (Year: 2009).*

(Continued)

*Primary Examiner* — Scott Long
*Assistant Examiner* — Paul C Martin
(74) *Attorney, Agent, or Firm* — Fish & Richardson, P.C.

(57) ABSTRACT

This document provides methods and materials involved in identifying mammals having lung adenocarcinoma characterized by neuroendocrine differentiation as well as methods and materials involved in treating mammals having lung adenocarcinoma characterized by neuroendocrine differentiation. For example, methods and materials for using ASCL1 and RET expression levels to identify lung cancer patients having lung adenocarcinoma characterized by neuroendocrine differentiation are provided.

10 Claims, 20 Drawing Sheets

Specification includes a Sequence Listing.

(56) References Cited

OTHER PUBLICATIONS

Tang et al. Artemin-Stimulated Progression of Human Non-Small Cell Lung Carcinoma Is Mediated by BCL2; Molecular Cancer Therapeutics, vol. 9, No. 6, pp. 1697-1708. (Year: 2010).*
Bhattacharjee et al., "Classification of human lung carcinomas by mRNA expression profiling reveals distinct adenocarcinoma subclasses," *Proc Natl Acad Sci U S A.*, 98(24):13790-13795, Epub Nov. 13, 2001.
Boldrini et al., "Epidermal growth factor receptor and K-RAS mutations in 411 lung adenocarcinoma: a population-based prospective study," *Oncol Rep.*, 22(4):683-691, Oct. 2009.
Borges et al., "An achaete-scute homologue essential for neuroendocrine differentiation in the lung," *Nature*, 386(6627):852-855, Apr. 24, 1997.
Bryant et al., "Clinically relevant characterization of lung adenocarcinoma subtypes based on cellular pathways: an international validation study," *PLoS One*, 5(7):e11712, Jul. 22, 2010.
Burton et al., "RET proto-oncogene is important for the development of respiratory $CO_2$ sensitivity," *J Auton Nerv Syst.*, 63(3):137-143, Apr. 14, 1997.
Chen et al., "Differentiation of medullary thyroid cancer by C-Raf-1 silences expression of the neural transcription factor human achaete-scute homolog-1," *Surgery*, 120(2):168-72; discussion 173, Aug. 1996.
Chikova et al., "Naturally occurring variants of human A9 nicotinic receptor differentially affect bronchial cell proliferation and transformation," *PLoS One.*, 6(11):e27978, Epub Nov. 18, 2011.
Dauger et al., "MASH-1/RET pathway involvement in development of brain stem control of respiratory frequency in newborn mice," *Physiol Genomics.*, 7(2):149-157, Dec. 21, 2001.
Dauger et al., "Ventilatory responses to hypercapnia and hypoxia in Mash-1 heterozygous newborn and adult mice," *Pediatr Res.*, 46(5):535-542, Nov. 1999.
Endoh et al., "Prognostic model of pulmonary adenocarcinoma by expression profiling of eight genes as determined by quantitative real-time reverse transcriptase polymerase chain reaction," *J Clin Oncol.*, 22(5):811-819, Mar. 1, 2004.
Freedman et al., "Cigarette smoking and subsequent risk of lung cancer in men and women: analysis of a prospective cohort study," *Lancet Oncol.*, 9(7):649-656, Epub Jun. 13, 2008.
Fujiwara et al., "ASCL1-coexpression profiling but not single gene expression profiling defines lung adenocarcinomas of neuroendocrine nature with poor prognosis," *Lung Cancer.*, 75(1):119-125, Epub Jul. 6, 2011.
GenBank® Accession No. NM_004316 (GI No. 190343011), "*Homo sapiens* achaete-scute complex homolog 1 (*Drosophila*) (ASCL1), mRNA," Dec. 18, 2011, 4 pages.
GenBank® Accession No. NM_020630 (GI No. 126273513), "*Homo sapiens* ret proto-oncogene (RET), transcript variant 4, mRNA," Feb. 27, 2012, 8 pages.
GenBank® Accession No. NM_020975 (GI No. 126273511), "*Homo sapiens* ret proto-oncogene (RET), transcript variant 2, mRNA," Feb. 27, 2012, 9 pages.
GenBank® Accession No. NP_004307 (GI No. 55743094), "achaete-scute homolog 1 [*Homo sapiens*]," Dec. 18, 2011, 3 pages.
GenBank® Accession No. NP_065681 (GI No. 10862701), "proto-oncogene tyrosine-protein kinase receptor Ret isoform c precursor [*Homo sapiens*]," Feb. 27, 2012, 4 pages.
GenBank® Accession No. NP_066124 (GI No. 10862703), "proto-oncogene tyrosine-protein kinase receptor Ret isoform a precursor [*Homo sapiens*]," Feb. 27, 2012, 5 pages.
Gilbert et al., "The aromatic-L-amino acid decarboxylase inhibitor carbidopa is selectively cytotoxic to human pulmonary carcinoid and small cell lung carcinoma cells," *Clin Cancer Res.*, 6(11):4365-4372, Nov. 2000.
Golub et al., "Molecular classification of cancer: class discovery and class prediction by gene expression monitoring," *Science.*, 286(5439):531-537, Oct. 15, 1999.
Herpel et al., "The cancer stem cell antigens CD133, BCRP1/ABCG2 and CD117/c-KIT are not associated with prognosis in resected early-stage non-small cell lung cancer," *Anticancer Res.*, 31(12):4491-500, Dec. 2011.
Hirsch et al., "Control of noradrenergic differentiation and Phox2a expression by MASH1 in the central and peripheral nervous system," *Development*, 125(4):599-608, Feb. 1998.
Huber et al., "Development of chromaffin cells depends on MASH1 function," *Development.*, 129(20):4729-4738, Oct. 2002.
Huber et al., "The role of Phox2B in chromaffin cell development," *Dev Biol.*, 279(2):501-508, Mar. 15, 2005.
International Preliminary Report on Patentability for PCT/US2014/022037, dated Sep. 17, 2015, 7 pages.
International Search Report and Written Opinion for PCT/US2014/022037, dated May 22, 2014, 16 pages.
Ionescu et al., "Nonsmall cell lung carcinoma with neuroendocrine differentiation—an entity of no clinical or prognostic significance," *Am J Surg Pathol.*, 31(1):26-32, Jan. 2007.
Kageyama et al., "Helix-loop-helix factors in growth and differentiation of the vertebrate nervous system," *Curr Opin Genet Dev.*, 7(5):659-665, Oct. 1997.
Kang et al., "Identification of genes with differential expression in acquired drag-resistant gastric cancer cells using high-density oligonucleotide microarrays," *Clin Cancer Res.*, 10(1 Pt 1):272-284, Jan. 1, 2004.
Khuder, "Effect of cigarette smoking on major histological types of lung cancer: a meta-analysis," *Lung Cancer*, 31(2-3):139-148, Feb.-Mar. 2001.
Kim et al., "A study of Ret proto-oncogene polymorphisms in association with lung cancer risk in the Korean population," *Anticancer Res.*, 30(9):3621-3627, Sep. 2010.
Klee et al., "Impact of sample acquisition and linear amplification on gene expression profiling of lung adenocarcinoma: laser capture micro-dissection cell-sampling versus bulk tissue-sampling," *BMC Med Genomics.*, 2:13, Mar. 9, 2009.
Kohno et al., "KIF5B-RET fusions in lung adenocarcinoma," *Nat Med.*, 18(3):375-377, Feb. 12, 2012.
Kosari et al., "Abstract 5251: ASCL1 and RET expression define a clinically relevant subgroup of lung adenocarcinoma characterized by neuroendocrine differentiation," *Cancer Res.*, Proceedings of the 105th Annual Meeting of the American Association for Cancer Research; Apr. 5-9, 2014; San Diego, CA. Philadelphia (PA): AACR; *Cancer Res.*, 74(19 Suppl):Abstract nr 5251, 2014.
Kosari et al., "ASCL1 and RET expression defines a clinically relevant subgroup of lung adenocarcinoma characterized by neuroendocrine differentiation," *Oncogene.*, 33(29):3776-3783, Epub Sep. 16, 2013.
Kouvaraki et al., "RET proto-oncogene: a review and update of genotype-phenotype correlations in hereditary medullary thyroid cancer and associated endocrine tumors," *Thyroid*, 15(6):531-544, Jun. 2005.
Kunnimalaiyaan et al., "Overexpression of the NOTCH1 intracellular domain inhibits cell proliferation and alters the neuroendocrine phenotype of medullary thyroid cancer cells," *J Biol Chem.*, 281(52):39819-39830, Epub Nov. 7, 2006.
Landi et al., "Gene expression signature of cigarette smoking and its role in lung adenocarcinoma development and survival," *PLoS One*, 3(2):e1651, Feb. 20, 2008.
Liang et al., "In vitro scratch assay: a convenient and inexpensive method for analysis of cell migration in vitro," *Nat Protoc.*, 2(2):329-333, 2007.
Linnoila et al., "Constitutive achaete-scute homologue-1 promotes airway dysplasia and lung neuroendocrine tumors in transgenic mice," *Cancer Res.*, 60(15):4005-4009, Aug. 1, 2000.
Lo et al., "MASH1 activates expression of the paired homeodomain transcription factor Phox2a, and couples pan-neuronal and subtype-specific components of autonomic neuronal identity," *Development*, 125(4):609-620, Feb. 1998.
Lodish et al., "RET oncogene in MEN2, MEN2B, MTC and other forms of thyroid cancer," *Expert Rev Anticancer Ther.*, 8(4):625-632, Apr. 2008.
Marsh et al., "Multiple endocrine neoplasia: types 1 and 2," *Adv Otorhinolaryngol.*, 70:84-90, Epub Feb. 24, 2011.

(56) References Cited

OTHER PUBLICATIONS

Massion et al., "Smoking-related genomic signatures in non-small cell lung cancer," *Am J Respir Crit Care Med.*, 178(11):1164-1172, Epub Sep. 5, 2008.

Miki et al., "Insights into the achaete-scute homolog-1 gene (hASH1) in normal and neoplastic human lung," *Lung Cancer*, 75(1):58-65, Jan. 2012.

Nishikawa et al., "miR-375 is activated by ASH1 and inhibits YAP1 in a lineage-dependent manner in lung cancer," *Cancer Res.*, 71(19):6165-6173, Epub Aug. 19, 2011.

Osada et al., "ASH1 gene is a specific therapeutic target for lung cancers with neuroendocrine features," *Cancer Res.*, 65(23):10680-10685, Dec. 1, 2005.

Osada et al., "Roles of achaete-scute homologue 1 in DKK1 and E-cadherin repression and neuroendocrine differentiation in lung cancer," *Cancer Res.*, 68(6):1647-1655, Mar. 15, 2008.

Poulsen et al., "A chimeric fusion of the hASH1 and EZH2 promoters mediates high and specific reporter and suicide gene expression and cytotoxicity in small cell lung cancer cells," *Cancer Gene Ther.*, 15(9):563-575, Epub Apr. 18, 2008.

Powell et al., "Gene expression in lung adenocarcinomas of smokers and nonsmokers," *Am J Respir Cell Mol Biol.*, 29(2):157-62. Epub Feb. 21, 2003.

Savci-Heijink et al., "The role of desmoglein-3 in the diagnosis of squamous cell carcinoma of the lung," *Am J Pathol.*, 174(5):1629-1637, Epub Mar. 26, 2009.

Shaw et al., "Clinical features and outcome of patients with non-small-cell lung cancer who harbor EML4-ALK," *J Clin Oncol.*, 27(26):4247-4253, Epub Aug. 10, 2009.

Shedden et al., "Gene expression-based survival prediction in lung adenocarcinoma: a multi-site, blinded validation study," *Nat Med.*, 14(8):822-827, Epub Jul. 20, 2008.

Shoba et al., "Retinoic acid influences the expression of the neuronal regulatory genes Mash-1 and c-ret in the developing rat heart," *Neurosci Lett.*, 318(3):129-132, Feb. 1, 2002.

Storey et al., "Statistical significance for genomewide studies," *Proc Natl Acad Sci U S A.*, 100(16):9440-9445, Epub Jul. 25, 2003.

Takahashi et al., "Clinicopathologic features of non-small-cell lung cancer with EML4-ALK fusion gene," *Ann Surg Oncol.*, 17(3):889-897, Mar. 2010.

Wang et al., "Achaete-scute complex homolog-1 promotes DNA repair in the lung carcinogenesis through matrix metalloproteinase-7 and O(6)-methylguanine-DNA methyltransferase," *PLoS One*, 7(12):e52832, Epub Dec. 26, 2012.

Wang et al., "RET fusions define a unique molecular and clinicopathologic subtype of non-small-cell lung cancer," *J Clin Oncol.*, 30(35):4352-4359, Epub Nov. 13, 2012.

Westerman et al., "Quantitative reverse transcription-polymerase chain reaction measurement of HASH1 (ASCL1), a marker for small cell lung carcinomas with neuroendocrine features," *Clin Cancer Res.*, 8(4):1082-1086, Apr. 2002.

Zarebczan et al., "Signaling mechanisms in neuroendocrine tumors as targets for therapy," *Endocrinol Metab Clin North Am.*, 39(4):801-810, Dec. 2010.

\* cited by examiner

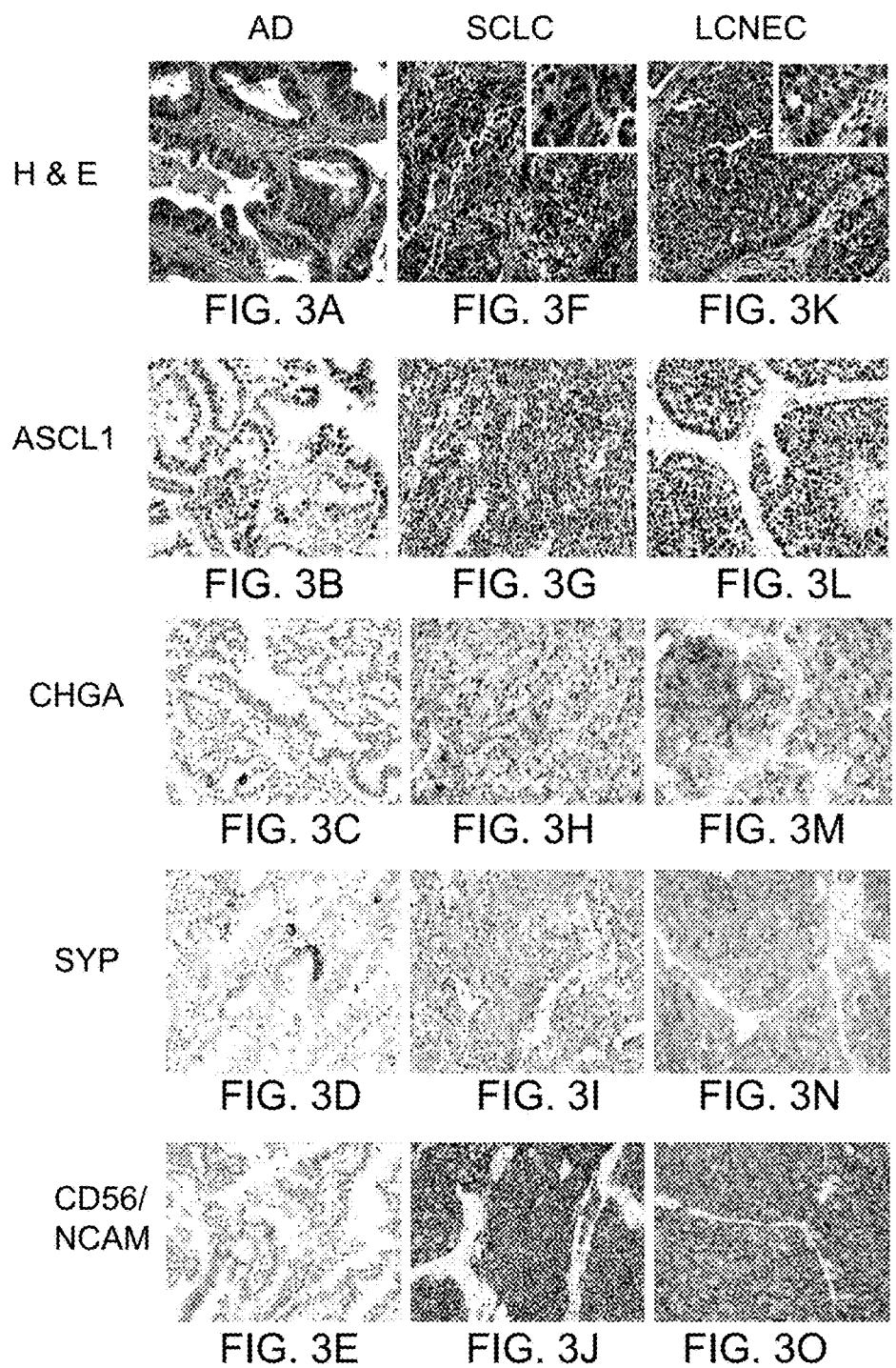

METHODS AND MATERIALS FOR IDENTIFYING AND TREATING MAMMALS HAVING LUNG ADENOCARCINOMA CHARACTERIZED BY NEUROENDOCRINE DIFFERENTIATION

CROSS-REFERENCE TO RELATED APPLICATIONS

This application is a continuation of U.S. application Ser. No. 14/773,488, filed Sep. 8, 2015 (Abandoned), which application is a National Stage application under 35 U.S.C. § 371 of International Application No. PCT/US2014/022037, filed Mar. 7, 2014, which claims the benefit of U.S. Provisional Application Ser. No. 61/775,316, filed Mar. 8, 2013. The disclosure of the prior application is considered part of (and is incorporated by reference in) the disclosure of this application.

BACKGROUND

1. Technical Field

This document relates to methods and materials involved in identifying mammals having lung adenocarcinoma characterized by neuroendocrine differentiation as well as methods and materials involved in treating mammals having lung adenocarcinoma characterized by neuroendocrine differentiation. For example, this document provides methods and materials for using achaete-scute homolog 1 (ASCL1) and RET expression levels to identify lung cancer patients having lung adenocarcinoma characterized by neuroendocrine differentiation.

2. Background Information

The clinical significance of neuroendocrine (NE) differentiation in lung adenocarcinoma, and the most appropriate biomarkers for this assessment, has been long debated. In the absence of a gold standard, investigators have most commonly used immunohistochemistry (IHC) of one or a combination of neuroendocrine markers, such as chromogranin (CHGA), synaptophysin (SYP), neuron-specific enolase (NSE), or neural cell adhesion molecule (CD56/NCAM) to assess the role of neuroendocrine differentiation in lung cancer survival.

SUMMARY

This document provides methods and materials involved in identifying mammals having lung adenocarcinoma characterized by neuroendocrine differentiation as well as methods and materials involved in treating mammals having lung adenocarcinoma characterized by neuroendocrine differentiation. For example, this document provides methods and materials for using ASCL1 and RET expression levels to identify lung cancer patients having lung adenocarcinoma characterized by neuroendocrine differentiation. As described herein, the presence of an elevated level of ASCL1 expression and an elevated level of RET within a lung cancer sample can indicate that a mammal (e.g., a human) has lung adenocarcinoma characterized by neuroendocrine differentiation. In some cases, the absence of an elevated level of ASCL1 expression and an elevated level of RET within a lung cancer sample can indicate that a mammal (e.g., a human) does not have lung adenocarcinoma characterized by neuroendocrine differentiation.

Having the ability to identify mammals as having lung adenocarcinoma characterized by neuroendocrine differentiation as described herein can allow those lung cancer patients to be properly identified and treated in an effective and reliable manner. For example, the lung cancer treatments provided herein can be used to treat lung cancer patients identified as having lung adenocarcinoma characterized by neuroendocrine differentiation.

In general, one aspect of this document features a method for identifying a mammal as having lung adenocarcinoma characterized by neuroendocrine differentiation. The method comprises, or consist essentially of, determining whether or not cancer cells from the mammal contain an elevated level of ASCL1 expression and an elevated level of RET expression, wherein the presence of the elevated level of ASCL1 expression and the presence of the elevated level of RET expression indicates that the mammal has lung adenocarcinoma characterized by neuroendocrine differentiation, and wherein the absence of the elevated level of ASCL1 expression and the absence of the elevated level of RET expression indicates that the mammal does not have lung adenocarcinoma characterized by neuroendocrine differentiation. The mammal can be a human. The elevated level can be determined using PCR. The elevated level can be determined using immunohistochemistry.

In another aspect, this document features a method for identifying a mammal as having lung adenocarcinoma characterized by neuroendocrine differentiation. The method comprises, or consists essentially of, (a) determining whether or not a lung cancer cells from the mammal contain an elevated level of ASCL1 expression and an elevated level of RET expression, (b) classifying the mammal as having lung adenocarcinoma characterized by neuroendocrine differentiation if the sample contains the elevated level of ASCL1 expression and the elevated level of RET expression, and (c) classifying the mammal as not having lung adenocarcinoma characterized by neuroendocrine differentiation if the sample lacks the elevated level of ASCL1 expression and the elevated level of RET expression. The mammal can be a human. The elevated level can be determined using PCR. The elevated level can be determined using immunohistochemistry.

In another aspect, this document features a method for identifying a mammal as having lung adenocarcinoma characterized by neuroendocrine differentiation, wherein the method comprises, or consists essentially of, (a) detecting the presence of an elevated level of ASCL1 expression and an elevated level of RET expression in lung cancer cells from the mammal, and (b) classifying the mammal as having lung adenocarcinoma characterized by neuroendocrine differentiation based at least in part on the presence of the elevated level of ASCL1 expression and the elevated level of RET expression. The mammal can be a human. The elevated level can be detecting using PCR. The elevated level can be detecting using immunohistochemistry.

In another aspect, this document features a method for treating lung cancer, wherein the method comprises, or consists essentially of, (a) detecting the presence of an elevated level of ASCL1 expression and an elevated level of RET expression in lung cancer cells from a mammal, and (b) administering a molecule to the mammal under conditions wherein the number of lung cancer cells within the mammal is reduced, wherein the molecule is selected from the group consisting of sunitinib, vandetanib, riluzole, alteplase, anistreplase, tenecteplase, sucralfate, dasatinib, pazopanib, tivozanib, OSI-930, telatinib, tandutinib, imatinib, sorafenib, levodopa, carbidopa, entacapone orion, L-dopa, ABT-089, mecamylamine, and succinylcholine.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 3A-P contain photographs and a heat graph of an immunohistochemical analysis. (A-E) AD characterized by ASCL1 mRNA expression (ASCL1$^+$ AD): (A) Adenocarcinoma with an acinar pattern. H&E. 400×; (B) ASCL1 protein expression (nuclear pattern, 70%, 2+). 400×; (C) CHGA (cytoplasmic pattern, 5%, 3+). 400×; (D) SYP (cytoplasmic pattern, 5%, 2+) 400×; and (E) CD56/NCAM (membranous pattern, 5%, 2+) 400×. (F-J) SCLC: (F) High-grade tumor characterized by extensive areas of necrosis and cells with high nuclear to cytoplasmic ratio, delicate nuclear chromatin and inconspicuous nucleoli. H&E 400×; (G) ASCL1 protein expression (nuclear pattern, 95%, 3+) 400×; (H) CHGA (cytoplasmic pattern, 100%, 2+) 400×; (I) SYP (cytoplasmic pattern, 100%, 1+) 400×; and (J) CD56/NCAM (membranous pattern, 100%, 2+) 400×. (K-O) LCNEC: (K) Poorly differentiated tumor with high mitotic activity (>10 mitotic figures/2 mm$^2$) and organoid nesting composed by cells with vesicular nuclei, evident nucleoli and moderate amount of cytoplasm. H&E, 400×; (L) ASCL1 protein expression (nuclear pattern, 95%, 3+) 400×; (M) CHGA (cytoplasmic pattern, 90%, 3+) 400×; (N) SYP (cytoplasmic pattern, 95%, 2+) 400×; and (O) CD56/NCAM (membranous pattern, 90%, 3+) 400×. (P) Heat map of IHC protein expression of ASCL1, CHGA, SYP, and CD56/NCAM.

μM, or 9 μM) for 14 days. FIG. 15 also contains a line graph plotting the viability of A549 cells and A549-ASCL1 cells 72 hours after treatment with the indicated amount of cisplatin. These results demonstrate that adenocarcinomas that express ASCL1 appear to be more resistant to treatment by cisplatin.

DETAILED DESCRIPTION

Figure 1:
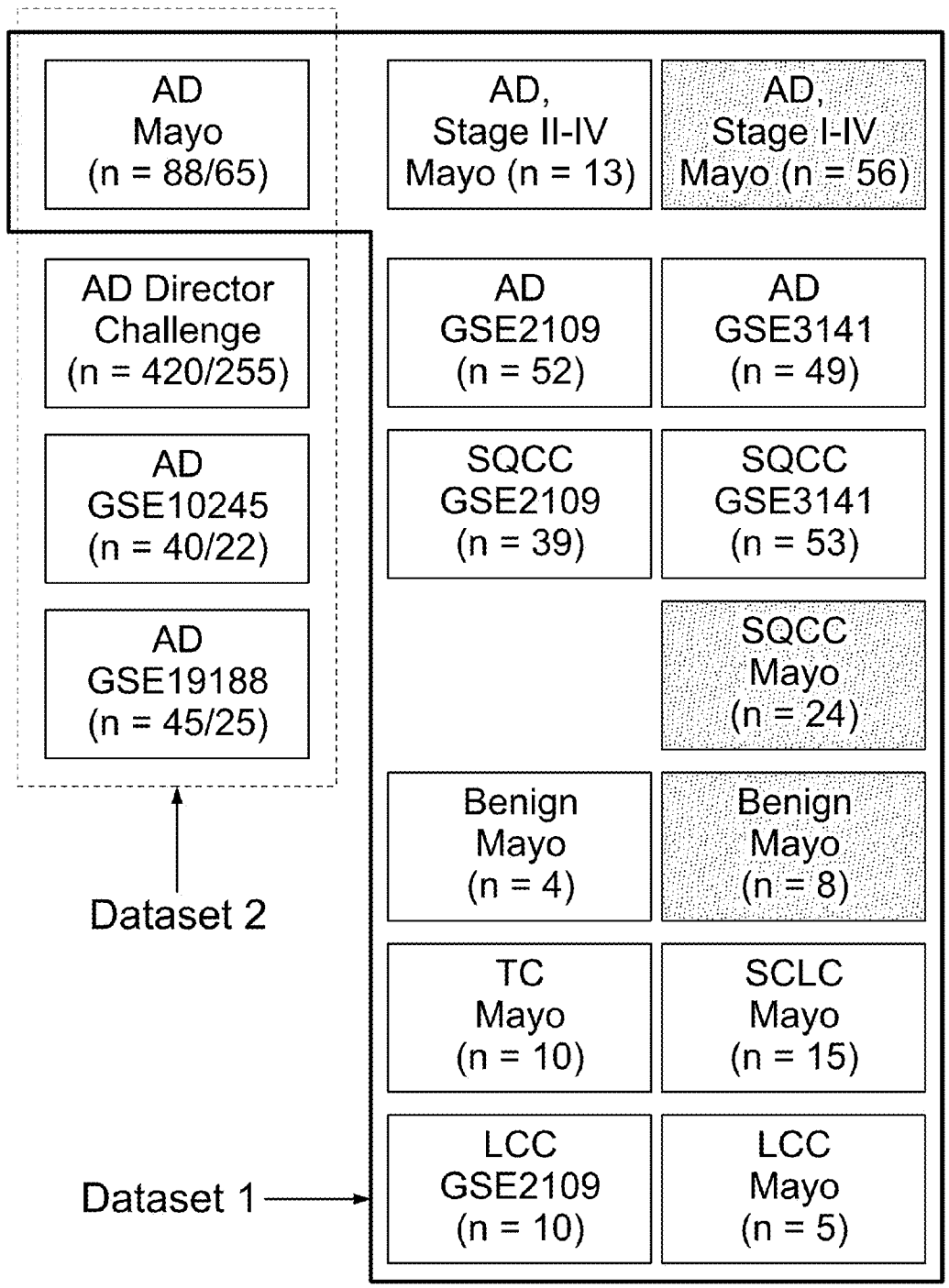
FIG. 1 is a schematic showing the composition of Datasets 1 and 2. Boxes with dotted shadings in Dataset I denote samples collected by laser capture microdissection (LCM). Numbers in parenthesis in Dataset 2 are all stages and stage 1 only sample sizes, respectively. Dataset 2 was used in survival analysis by RET. All samples in this dataset were collected in bulk.

This document provides methods and materials related to identifying mammals having lung adenocarcinoma characterized by neuroendocrine differentiation. For example, this document provides methods and materials for identifying mammals (e.g., humans) as having lung adenocarcinoma characterized by neuroendocrine differentiation by determining whether or not a lung cancer sample (e.g., lung tissue biopsy) from the mammal contains cancer cells having an elevated level of ASCL1 expression and/or an elevated level of RET expression. As described herein, if a mammal contains lung cancer cells with an elevated level of ASCL1 expression and/or an elevated level of RET expression, then that mammal can be classified as having lung adenocarcinoma characterized by neuroendocrine differentiation. If a mammal contains a lung cancer cells that lack an elevated level of ASCL1 expression and lack an elevated level of RET expression, then that mammal can be classified as not having lung adenocarcinoma characterized by neuroendocrine differentiation.

The term "elevated level" as used herein with respect to a level of expression (e.g., ASCL1 and/or RET expression) refers to any level that is greater than a reference level for that molecule (e.g., a reference level of ASCL1 and/or RET expression). The term "reference level" as used herein with respect to a particular molecule (e.g., a reference level of ASCL1 and/or RET expression) refers to the level of expression that is typically observed with normal healthy lung cells or lung adenocarcinoma characterized by a lack of neuroendocrine differentiation from mammals (e.g., humans). For example, a reference level of ASCL1 expression can be the average level of ASCL1 expression that is present in lung cells obtained from a random sampling of 50 humans free of lung cancer. In some cases, an elevated level of expression (e.g., ASCL1 and/or RET expression) can be a level that is at least 10, 25, or 50 percent greater than a reference level for that molecule (e.g., a reference level of ASCL1 and/or RET expression). In some cases, an elevated level of ASCL1 expression or RET expression can be a detectable level (e.g., an expression level detectable by immunocytochemistry). It will be appreciated that levels from comparable samples are used when determining whether or not a particular level is an elevated level.

As described herein, the level of ASCL1 and/or RET expression within lung cancer cells can be used to determine whether or not a particular mammal has lung adenocarcinoma characterized by neuroendocrine differentiation. Any appropriate lung cancer sample can be used as described herein to identify mammals having lung adenocarcinoma characterized by neuroendocrine differentiation. For example, lung cancer tissue samples, lung cancer cell samples, and lung cancer needle biopsy specimen can be used to determine whether or not a mammal has lung adenocarcinoma characterized by neuroendocrine differentiation.

In addition, any appropriate method can be used to obtain lung cancer cells. For example, a lung cancer sample can be obtained by a tissue biopsy or following a surgical resection. Once obtained, a sample can be processed prior to measuring a level of expression. For example, a lung cancer sample can be processed to extract RNA from the sample. Once obtained, the RNA can be evaluated to determine the level of an mRNA of interest. In some embodiments, nucleic acids present within a sample can be amplified (e.g., linearly amplified) prior to determining the level of expression (e.g., using array technology). In another example, a lung cancer sample can be frozen, and sections of the frozen tissue sample can be prepared on glass slides. The frozen tissue sections can be stored (e.g., at −80° C.) prior to analysis, or they can be analyzed immediately (e.g., by immunohistochemistry with an antibody specific for a particular polypeptide of interest).

Any appropriate methods can be used to determine the level of ASCL1 and/or RET expression within lung cancer cells. For example, quantitative real time PCR, in situ hybridization, or microarray technology can be used to determine whether or not a particular sample contains an elevated level of mRNA expression for a particular nucleic acid or lacks an elevated level of mRNA expression for a particular nucleic acid. In some cases, the level of expression can be determined using polypeptide detection methods such as immunochemistry techniques. For example, antibodies specific for ASCL1 and/or RET polypeptides can be used to determine the polypeptide level in a sample. In some cases, polypeptide-based techniques such as ELISAs and immunocytochemistry techniques can be used to determine whether or not a particular sample contains an elevated level of polypeptide expression for a particular nucleic acid or lacks an elevated level of polypeptide expression for a particular nucleic acid.

Examples of a human ASCL1 nucleic acid can have the sequence set forth in GenBank® Accession No. NM_004316 (GI No. 190343011), and a human ASCL1 polypeptide can have the sequence set forth in GenBank® Accession No. NP_004307 (GI No. 55743094). Examples of a human RET nucleic acid can have the sequence set forth in GenBank® Accession No. NM_020630 (GI No. 126273513) or NM_020975 (GI No. 126273511), and a human RET polypeptide can have the sequence set forth in GenBank® Accession No. NP_065681 (GI No. 10862701) or NP_066124 (GI No. 10862703).

Once the level of ASCL1 and/or RET expression within lung cancer cells from a mammal is determined, the level(s) can be compared to reference level(s) and used to classify the mammal as having or lacking lung adenocarcinoma characterized by neuroendocrine differentiation as described herein.

This document also provides methods and materials to assist medical or research professionals in identifying a mammal as having lung adenocarcinoma characterized by neuroendocrine differentiation. Medical professionals can be, for example, doctors, nurses, medical laboratory technologists, and pharmacists. Research professionals can be, for example, principle investigators, research technicians, postdoctoral trainees, and graduate students. A professional can be assisted by (a) determining the level of ASCL1 and/or RET expression within lung cancer cells, and (b) communicating information about that the level(s) to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides methods and materials for treating lung adenocarcinoma characterized by neuroendocrine differentiation. For example, one or more molecules listed in Table 1, 2, or 3 can be administered to a mammal (e.g., a human) having lung adenocarcinoma characterized by neuroendocrine differentiation under conditions wherein the presence or progression of the lung adenocarcinoma characterized by neuroendocrine differentiation is reduced. For example, a molecule listed in Table 1 such as tedisamil can be administered to a human having lung adenocarcinoma characterized by neuroendocrine differentiation such that the number of lung adenocarcinoma cells within the human is reduced. In some cases, one or more of molecules listed in Table 2A or 2B can be administered in combination with one or more of molecules listed in Table 1 to treat lung adenocarcinoma characterized by neuroendocrine differentiation. For example, tedisamil can be administered in combination with riluzole to a human having lung adenocarcinoma characterized by neuroendocrine differentiation.

TABLE 1

Molecules for treating lung adenocarcinoma characterized by neuroendocrine differentiation.

| Gene | Molecule | Dosage Range (mg/kg) |
| --- | --- | --- |
| ADRA2A | Paliperidone | 6-12 mg daily oral, 117 monthly if injectable but can vary 39-234 mg |
| FGB | sucralfate | 1 g (e.g., 10 mL/2 teaspoonfuls) four times per day |
| TUBB2B | Brentixumab vedotin | 1.8 mg/kg administered as an intravenous infusion over 30 minutes every 3 weeks |
| TUBB2B | cabazitaxel | 20 to 25 mg/m² administered as a one-hour intravenous infusion every three weeks |
| KCNMB4 | tedisamil | 0.5-4 mg/kg, i.v. |

TABLE 2A

Molecules that can be used in combination with one or more molecules listed in Table 1 for treating lung adenocarcinoma characterized by neuroendocrine differentiation.

| Gene | Molecule | Dosage Range (mg/kg) |
| --- | --- | --- |
| RET | sunitinib | 30 mg/kg |
| RET | vandetanib | 60 mg/kg |
| SCN3A | riluzole | 40-60 mg twice daily |
| FGA | Alteplase | 0.9 mg/kg, and a total not exceeding 90 mg |
| FGA | Anistreplase | IV 30 units over 2 to 5 min into IV line or vein |
| FGA | Tenecteplase | less than 60 kg: 30 mg IV bolus administered over 5 seconds. 60 to less than 70 kg: 35 mg IV bolus administered over 5 seconds 70 to less than 80 kg: 40 mg IV bolus administered over 5 seconds 80 to less than 90 kg: 45 mg IV bolus administered over 5 seconds 90 kg or greater: 50 mg IV bolus administered over 5 seconds) |
| FGA | Sucralfate | 1 g (10 mL/2 teaspoonfuls) four times per day |
| KIT | Dasatinib | 100-180 mg once daily |
| KIT | sunitinib | 30 mg/kg |
| KIT | pazopanib | 400-800 mg orally once daily |
| KIT | tivozanib | 1-2 mg daily |
| KIT | OSI-930 | 500 mg twice a day |
| KIT | Telatinib | 20 mg once daily to 1,500 mg twice daily |
| KIT | tandutinib | 50 mg to 700 mg twice daily |
| KIT | imatinib | 400-800 mg a day |
| KIT | sorafenib | 400-800 mg a day |
| DDC | Levodopa/Carbidopa/Entacapone Orion | 200 mg/50 mg/200 mg dose is 7 tablets per day (maximum dose a day) |
| DDC | carbidopa/levodopa | 1 tablet of carbidopa 25 mg/levodopa 100 mg orally 3 times a day, or 1 tablet of 10 mg carbidopa/100 mg levodopa orally 3 to 4 times a day. The dose may be increased by 1 tablet orally every 1 to 2 days to a dose of 8 tablets/day (2 tablets orally 4 times a day) |
| DDC | Carbidopa | 70-100 mg a day |
| DDC | L-Dopa | 100-500 mg |
| CHRNA9 | ABT-089 | 1-50 mg |
| CHRNA9 | mecamylamine | 2-25 mg |
| CHRNA9 | succinylcholine | 0.3-2.0 mg/kg |

TABLE 2B

Molecules that can be used to reduce or inhibit the activity of polypeptides encoded by the listed genes.

| Gene | Molecule |
| --- | --- |
| KCNMB4 | tedisamil |
| RET | sunitinib, vandetanib |
| SCN3A | riluzole |
| ADRA2A | paliperidone, risperidone, antazoline/naphazoline, acetaminophen/clemastine/pseudoephedrine, articaine/epinephrine, bupivacaine/epinephrine, caffeine/ergotamine, acetaminophen/dexbrompheniramine/pseudoephedrine, dapiprazole, dexbrompheniramine/pseudoephedrine, chlorpheniramine/ibuprofen/pseudoephedrine, dipivefrin, cetirizine/pseudoephedrine, asenapine, epinephrine/prilocaine, epinephrine/lidocaine, PYM-50018, V2006, lurasidone, paliperidone palmitate, fexofenadine/pseudoephedrine, guaifenesin/phenylpropanolamine, oxymetazoline, prazosin, phenylpropanolamine, ephedrine, tolazoline, guanfacine, guanabenz, guanethidine, phenoxybenzamine, |

TABLE 2B-continued

Molecules that can be used to reduce or inhibit the activity of polypeptides encoded by the listed genes.

| Gene | Molecule |
|---|---|
|  | dexmedetomidine, UK 14304, clonidine, dexefaroxan, quinidine, polythiazide/prazosin, chlorothiazide/methyldopa, chlorthalidone/clonidine, propafenone, guanadrel, hydrochlorothiazide/methyldopa, metaraminol, tizanidine, quetiapine, D-pseudoephedrine, apraclonidine, venlafaxine, phentolamine, labetalol, mephentermine, propylhexedrine, yohimbine, dihydroergotamine, ergotamine, norepinephrine, alpha-methyl dopa, epinephrine, dopamine, chlorpheniramine/phenylpropanolamine, desloratadine/pseudoephedrine, acrivastine/pseudoephedrine, carbinoxamine/pseudoephedrine, brompheniramine/codeine/phenylpropanolamine, pseudoephedrine/triprolidine, codeine/pseudoephedrine/triprolidine, carbetapentane/chlorpheniramine/ephedrine/phenylephrine, brompheniramine/dextromethorphan/pseudoephedrine, chlorpheniramine/hydrocodone/pseudoephedrine, azatadine/pseudoephedrine, naphazoline, carbinoxamine/dextromethorphan/pseudoephedrine |
| FGA | F2 |
| FGB | F2 |
| KIT | dasatinib, sunitinib, pazopanib, tivozanib, OSI-930, telatinib, tandutinib, imatinib, sorafenib |
| DDC | carbidopa/entacapone/levodopa, carbidopa/levodopa, S(−)-carbidopa, L-dopa |
| TUBB2B | brentuximab vedotin, cabazitaxel |
| CHRNA9 | ABT-089, isoflurane, mecamylamine, succinylcholine, rocuronium, doxacurium, amobarbital, mivacurium, pipecuronium, rapacuronium, metocurine, atracurium, cisatracurium, acetylcholine, nicotine, D-tubocurarine, arecoline, enflurane, pancuronium, vecuronium |

The invention will be further described in the following examples, which do not limit the scope of the invention described in the claims.

EXAMPLES

Example 1

Elevated ASCL1 and RET Expression can be Used to Identify Patients with Lung Adenocarcinoma Characterized by Neuroendocrine Differentiation Patient Sample Population Using the Mayo Clinic frozen tumor bank, lung specimens resected from 303 patients between 1997 and 2007 were selected. Neoadjuvant therapy was not given to any patient included in this study. Formalin-fixed paraffin-embedded H&E sections from the corresponding surgical specimens were reviewed, and the diagnoses were confirmed according to the 2004 World Health Organization classification of tumors. Bronchioloalveolar carcinoma variant of lung adenocarcinoma (AD) was excluded; hence, all ADs analyzed were clearly and predominantly invasive tumors. Never-smokers (NS) were characterized by less than 100 cigarettes per lifetime. Samples exclusively from NS (n=130) were analyzed on the Illumina platform, and samples from former and current smokers (S) patients (n=186) and NS (n=18) were analyzed on the Affymetrix platform. Table 3 describes the clinicopathologic features of the samples.

TABLE 3

Clinicopathologic features of samples used.

|  | Samples arrayed on the Affymetrix platform | Samples arrayed on the DASL platform |
|---|---|---|
| Age at diagnosis (median, range) | 69 yrs, 31-93 yrs | 67 yrs, 17-91 yrs |
| Sex |  |  |
| Male | 94 | 24 |
| Female | 92 | 82 |
| Smoking status |  |  |
| Smoker | 166 | 0 |
| Never-smoker | 18 | 106 |
| Not Available | 2 | 0 |
| Histological analysis |  |  |
| Adenocarcinoma (AD) | 132 | 70 |
| Adeno-squamous | 0 | 6 |
| Squamous cell carcinoma (SQCC) | 24 | 2 |
| Small cell carcinoma (SCLC) | 15 | 0 |
| Large cell carcinoma (LCC) | 5 | 0 |
| Typical carcinoid (TC) | 10 | 24 |
| Atypical carcinoid (AC) | 0 | 4 |
| Non-neoplastic lung tissue (N) | 12 | 118 |

Immunohistochemical (IHC) Analysis

IHC procedures for ASCL1, CHGA, SYP, CD56/NCAM, and RET were as follows. A representative formalin fixed paraffin embedded (FFPE) block from a subset of gene expression profiled lung tumors of smokers (S), consisting of adenocarcinoma (AD) (n=83), small cell lung carcinoma (SCLC) (n=12), large cell carcinoma (LCC) (n=4), and large cell neuroendocrine carcinoma (LCNEC) (n=2), was selected. The analysis was limited to S as NE differentiation was significantly more prevalent in this group of tumors. IHC studies using antibodies directed against ASCL1/MASH1 (monoclonal, clone 24B72D11.1, 1:50 dilution, BD/Pharmingen, San Diego, Calif.), CHGA (monoclonal, clone LK2H10, 1:500 dilution, Chemicon/Millipore, Billerica, Mass.), SYP (monoclonal, clone SY38, 1:40 dilution, ICN, Irvine, Calif.), and CD56/NCAM (monoclonal clone 123C3, 1:25 dilution, Monosan, Uden, the Netherlands) were performed. The IHC stains were detected by the Dako Advance polymer-based detection system (Dako, Carpenteria, Calif., U.S.) using the Dako Autostainer. For each IHC assay, a positive control and negative control were performed. Immunostained slides were reviewed and scored by two pathologists, who were blinded to the corresponding microarray data. A consensus score was achieved for all cases. Cases were considered immunoreactive when exhibiting 5% or more tumor cells showing a nuclear staining pattern for ASCL1, a clear granular cytoplasmic staining pattern for CHGA and SYP, and a distinct membranous staining pattern for CD56/NCAM.

Similarly, twenty nine AD samples (14 ASCL1[+] and 15 ASCL1[−]) with microarray expression data were selected for RET IHC using 1:500 dilutions of Epitomics 3454-1 rabbit monoclonal antibody. An ASCL1/RET co-IHC was developed by DAB staining for ASCL1 first (1:100 dilution monoclonal, clone 24B72D11.1, BD/Pharmingen, San Diego, Calif.) and then Fast Red staining (1:500 dilutions of Epitomics 3454-1 rabbit monoclonal antibody) for RET.

Immunoreactivity was semi-quantitatively scored based on a) the percentage of positive tumor cells (Labeling index, LI), ranging from 0 to 100%, in increments of 5%; and b) the intensity of staining, graded as: weak +1, moderate +2, and strong +3. For a comparative analysis of NE markers (ASCL1, CHGA, SYP, and CD56/NCAM), the $\text{Log}_2$ of the product of the percentage of positive tumor cells (Labeling index, LI) multiplied by the intensity of staining was determined for each IHC NE marker and used to generate a heat map of the IHC NE markers using 'heatmap' function in the open source package R version 2.12.2 (World Wide Web at "r-project.org/"). RET IHC frequently had areas with different intensity of stains. In each case, RET IHC score was computed as the summation of $\text{Log}_2$ (LI)×intensity for each stained area.

Preparation of Samples for Expression Profiling on the Affymetrix Platform

Lung tumor cells and non-neoplastic cells were collected by either laser capture microdissection (LCM=86) or macrodissection (M=112) to assure high tumor content (>80%) as described elsewhere (Klee et al., *BMC Med. Genomics*, 2:13 (2009)). Total RNA from samples collected by LCM was isolated using the Micropure kit (Qiagen Corp, Valencia, Calif.) as described elsewhere (Savci-Heijink et al., *Am. J. Pathol.*, 174(5):1629-37 (2009)). Briefly, RNA quality and quantity were controlled by the Agilent bioanalyzer and the Ribogreen assay or by a quantitative PCR assay based on the ratio of concentration of 3' to middle transcript of β-actin. Total RNA (10 ng) from these LCM-collected samples were labeled in a two round linear amplification/labeling process according to the Small Sample Preparation protocol (Affymetrix Corp, Santa Clara, Calif.). Affymetrix arrays were scanned according to the manufacturer's protocol. Total RNA from samples obtained by macrodissection was isolated using the RNeasy kit (Qiagen). The quality and quantity of RNA samples were controlled by the Agilent bioanalyzer and a NanoDrop spectrophotometer. Total RNA (1.2 µg) was labeled according to the standard Affymetrix protocol. Labeled cRNA was hybridized to U133PLUS2 chipset.

Preparation of Samples for Expression Profiling on the Illumina Platform

RNA from macrodissected samples were purified by the RNeasy kit (Qiagen) and analyzed by the Agilent bioanalyzer and a NanoDrop spectrophotometer. For the WG-DASL assay (Illumina, San Diego, Calif.), total RNA (100 ng) was reverse transcribed with biotinylated primers. The resulting cDNA was annealed to chimeric query oligonucleotides, which contained a gene-specific region and a universal primer sequence for PCR amplification, and then bound to streptavidin-conjugated paramagnetic particles. The gene-specific oligonucleotides were extended by second-strand cDNA synthesis and then ligated. Subsequently, the products were sequestered by magnetic separation, washed to remove unbound molecules, and then amplified by PCR with fluorophore-labeled universal primers. The resulting PCR products were purified, applied to Human-Ref-8 v3 beadchips, and then hybridized for 16 hours at 58° C. The beadchips were washed and scanned in a BeadArray Reader using BeadScan v3 software (Illumina).

Microarray Data Analysis

Normalized expression values from WG-DASL experiments were generated by the Bead Studio software (Illumina). Affymetrix intensity files (.CEL files) were processed and normalized by the 'gcrma' package in R. All subsequent analyses of DASL and Affymetrix data were carried out in R. Other than data generated at Mayo, expression analysis included various publically available Affymetrix datasets. Two major datasets which were a compendium of smaller datasets and frequently used in this study were named Dataset 1 and Dataset 2. Compositions of these two sets are shown in FIG. 1. AD and LCC samples with high expression of either DSG3 or KRT5 (squamous differentiation markers) were excluded. Similarly, squamous cell carcinoma (SQCC) samples with low expression of DSG3 and KRT5 were excluded. Pearson correlation coefficients between various NE markers were calculated by 'cor.test,' and a heatmap of all samples in Dataset 1 was generated by the 'heatmap' function.

Differentially Expressed Transcripts Between ASCL1$^+$ and ASCL1$^-$ Tumors

Dataset 2 (FIG. 1) was used to examine the expression differences between ASCL1$^+$ and ASCL1$^-$ tumors in stage I AD. All files had follow up information. Array files (n=593) with more than 22,000 common Affymetrix probesets were included in this dataset. The microarray signal intensity (.CEL) files were normalized and processed by the "gcrma" package in R. Threshold for ASCL1 status (+ or −) was chosen as before using 209988_s_at probeset at $\text{Log}_2$ intensity of 8. To identify most differentially expressed genes in ASCL1$^+$ versus ASCL1$^-$ tumors, probesets were ranked by signal to noise ratio calculated as $\text{SNR}=(\mu_{ASCL1+}-\mu_{ASCL1-})/(\sigma_{ASCL1+}+\sigma_{ASCL1-})$ where µ's were mean expression values and σ's were maximum of 0.2×µ and standard deviation (Golub et al., *Science*, 286(5439):531-7 (1999)). SNR values greater than and less than zero potentially indicate over and under expression in ASCL1$^+$ compared with ASCL1$^-$ tumors, respectively. It was also required in this example that the average expression in samples over-expressing a gene had greater than 3.5 $\text{Log}_2$ intensities. $\text{Log}_2$ expression intensities for the gcrma normalized data ranged from 2 to 15. Based on experience with quantitative RT-PCR, gene expression intensities below 3.5 were not reliable and frequently not detected. Significant figures for over-expression in ASCL1$^+$ compared with ASCL1$^-$ tumors were calculated by t-test and then corrected for multiple comparison correction using the 'qvalue' package in R (Storey et al., *Proc. Natl. Acad. Sci. USA*, 100(16):9440-5 (2003)).

Survival Analysis

Figure 2:
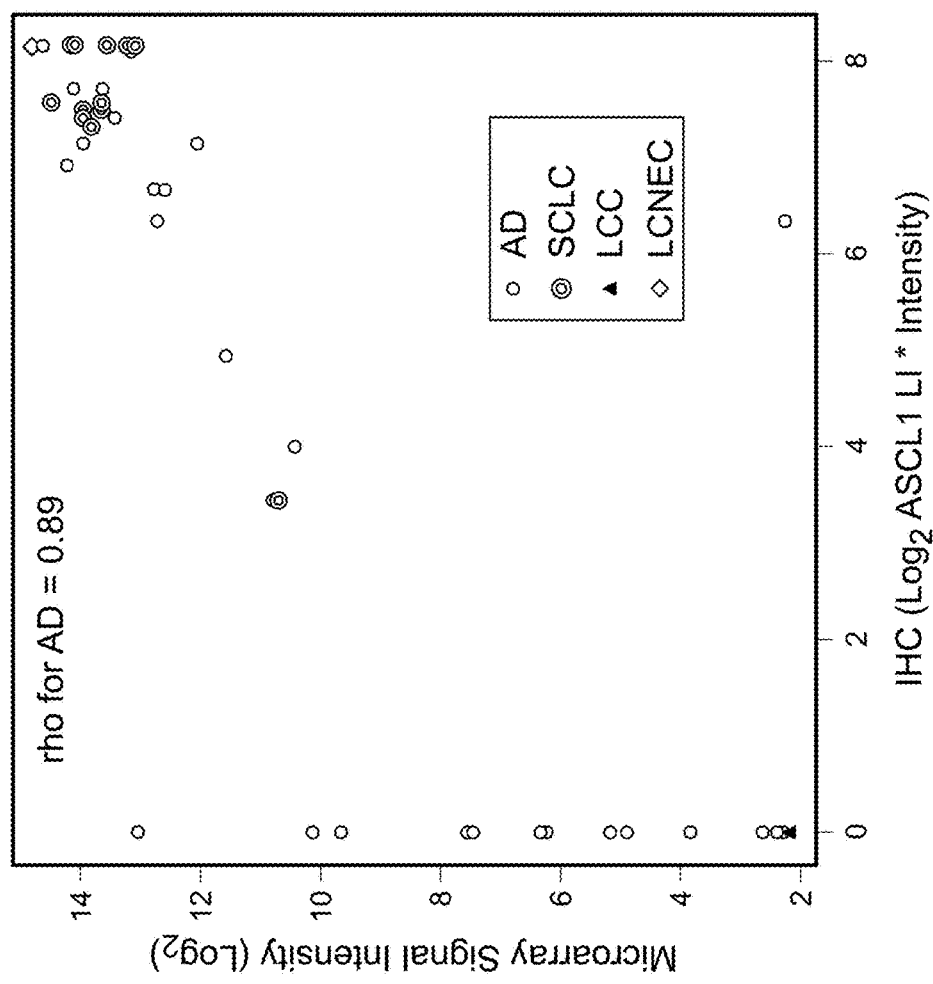
FIG. 2 is a graph plotting the threshold selection for ASCL1 positive and negative status. With minor exceptions, signal intensities at or above 8 produced a positive staining on the IHC. There was a strong Pearson's correlation (rho=0.89) between the Labeling index (LI) and microarray signal intensities ($Log_2$).

Given that only 15-20% of AD expresses ASCL1, any one dataset by itself did not provide sufficient samples for statistical analysis. Therefore, the Mayo dataset (n=132) was combined with four other lung AD microarray datasets that had follow up information available. These included the Director's Challenge dataset (Shedden et al., *Nat. Med.*, 14(8):822-7 (2008)) (n=420), Bhattarcharjee dataset (Bhattacharjee et al., *Proc. Natl. Acad. Sci. USA*, 98(24):13790-5 (2001)) (n=139), Kune dataset (GEO dataset GSE10245, n=40), and Hou dataset (GEO dataset GSE19188, n=45). With the exception of Bhattarcharjee dataset, all other array files had common probesets for ASCL1, and the most variable probeset in all sets (209988_s_at) was chosen to determine the expression levels of ASCL1. Based on the IHC data, expression levels above signal intensity 8 ($\text{Log}_2$) were chosen as the threshold for ASCL1$^+$ and ASCL1$^-$ status (FIG. 2). The range of microarray $\text{Log}_2$ signal intensities for this probeset was 2-15. Therefore, signal intensity of 8 or higher corresponded to a moderate to high expression level in the 85th percentile and higher. The ASCL1 status in the Bhattarcharjee dataset was determined by inspecting ASCL1 expression histograms and selecting thresholds breakpoints at the 85 percentile. Survival analyses used the "survival" package in R (http at "//cran.at.r-project.org") and included time to progression and overall survival stratified by stage. In the combined dataset, differences in survival times between ASCL1$^-$ and ASCL1$^+$ tumors for stage I patients who died was assessed by a group t-test. A subset of 11 AD in the Director's Challenge data with high expression of CHGA, SCG2, CHGB, NCAM1 (CD56), or SYP were identified as large cell NE carcinomas (LCNEC) after histologic review (Bryant et al., PLoS One, 5(7):e11712 (2010)). In light of this finding, the cases of AD in this study were re-reviewed, and the diagnosis confirmed by morphology. Furthermore, in the Director's Challenge data, 19 cases were identified with high expression of at least one of these NE markers which could have represented LCNEC and thus NSCLC with poorer prognosis. A group t-test was repeated after excluding these samples, but did not alter the overall results and conclusions. In the analysis of overall survival, the proportional hazard assumption for stage I tumors was tested by the "cox.zph" routine in the "survival" package. A small p-value indicated non-proportional hazard. Proportional hazard assumption was tested after censoring follow up times at five and more years.

Associations Between RET Expression and Survival in ASCL1+ Tumors

By Cox proportional hazards regression analysis in R (coxph), two probesets corresponding to the RET oncogene (215771_x_at, 205879_x_at) had significant associations with overall survival in stage I AD after the follow up data at 5 years was censored. To visualize this association by a Kaplan Meir (KM) plot, varying the threshold for "low" and "high" expression levels of RET (215771_x_at) was examined. Values in 3.0 to 6.5 were significant with p values ranging 0.0005 to 0.029. Excluding AD samples where an alternative diagnosis of LCNEC was possible did not appreciably change these results (Bryant et al., PLoS One, 5(7): e11712 (2010)). The reported KM plot used a threshold of 3.5, as signal intensities below this threshold are usually not detected by RT-PCR. If the data was not censored at 5 years, p-values ranged from 0.00053 to 0.037 as the threshold changed from 3.0 to 6.5. Same probeset and threshold was used in the KM plot of all AD stages. Also, a KM plot for RET stains was generated by using the mean of all RET IHC scores as the threshold for selecting "low" and "high" levels.

Gene Set Analysis

To find gene sets enriched in ASCL1+ tumors compared with ASCL1− tumors, probesets (13166) with SNR greater or less than zero were used in the GSA package in R and using Molecular Signatures Database (MSigDB) version 3.0. The analysis used 500 permutations and an FDR default value of 0.05. For robustness, 20 iterations were performed, and gene sets identified in at least 16 iterations (80%) were reported. To find gene sets associated with aggressive behavior in ASCL1+ tumors, these tumors were divided into aggressive and non-aggressive groups. Aggressive tumors were from patients who died in less than 3.5 years after surgery (n=21) and non-aggressive tumors were from patients who survived 6 or more years after surgery (n=20). Probesets (13126) with SNR greater or less than zero in comparisons of aggressive versus non-aggressive tumors were used in the GSA program with the same selection criteria as above.

Comparative IHC Analysis of NE Markers (ASCL1, CHGA, SYP and CD56/NCAM)

Immunostaining quality of ASCL1, CHGA, SYP, and CD56/NCAM was comparable, and all slides were interpretable. Scattered immunoreactive bronchiolar basal-located NE cells were considered as positive internal controls for the IHC reaction. Labeling indices (LIs) and immunoreactivity for ASCL1, CHGA, SYP, and CD56/NCAM for AD, SCLC, LCNEC and LCC are shown in Table 4.

TABLE 4

Detailed results of the immunohistochemical study for ASCL1 and other NE markers in all lung cancer subtypes.

| SUBTYPE | | AD | SCLC | LCNEC | LCC |
|---|---|---|---|---|---|
| No. of patients | | 83 | 12 | 2 | 4 |
| ASCL1 | LI mean +/− SD | 54.4 +/− 29 | 84.6 +/− 25.6 | 95 +/− 0 | 0 |
| | Range | 5-95 | 5-95 | 95 | 0 |
| | Immunoreactive cases | 15/83 (18%) | 12/12 (100%) | 2/2 (100%) | 0/4 (0%) |
| CHGA | LI mean +/− SD | 42.5 +/− 40.2 | 74.6 +/− 31.4 | 55 +/− 49.5 | 0 |
| | Range | 5-85 | 50-100 | 20-90 | 0 |
| | Immunoreactive cases | 4/83 (5%) | 11/12 (92%) | 2/2 (100%) | 0/4 (0%) |
| SYP | LI mean +/− SD | 31.3 +/− 32.8 | 90.4 +/− 20.5 | 95 +/− 0 | 0 |
| | Range | 5-100 | 20-100 | 95 | 0 |
| | Immunoreactive cases | 20/83 (24%) | 12/12 (100%) | 2/2 (100%) | 0/4 (0%) |
| CD56/NCAM | LI mean +/− SD | 26 +/− 29 | 92.9 +/− 13.9 | 92.5 +/− 3.5 | 0 |
| | Range | 5-75 | 50-100 | 90-95 | 0 |
| | Immunoreactive cases | 5/83 (6%) | 12/12 (100%) | 2/2 (100%) | 0/4 (0%) |

Figure 3P:
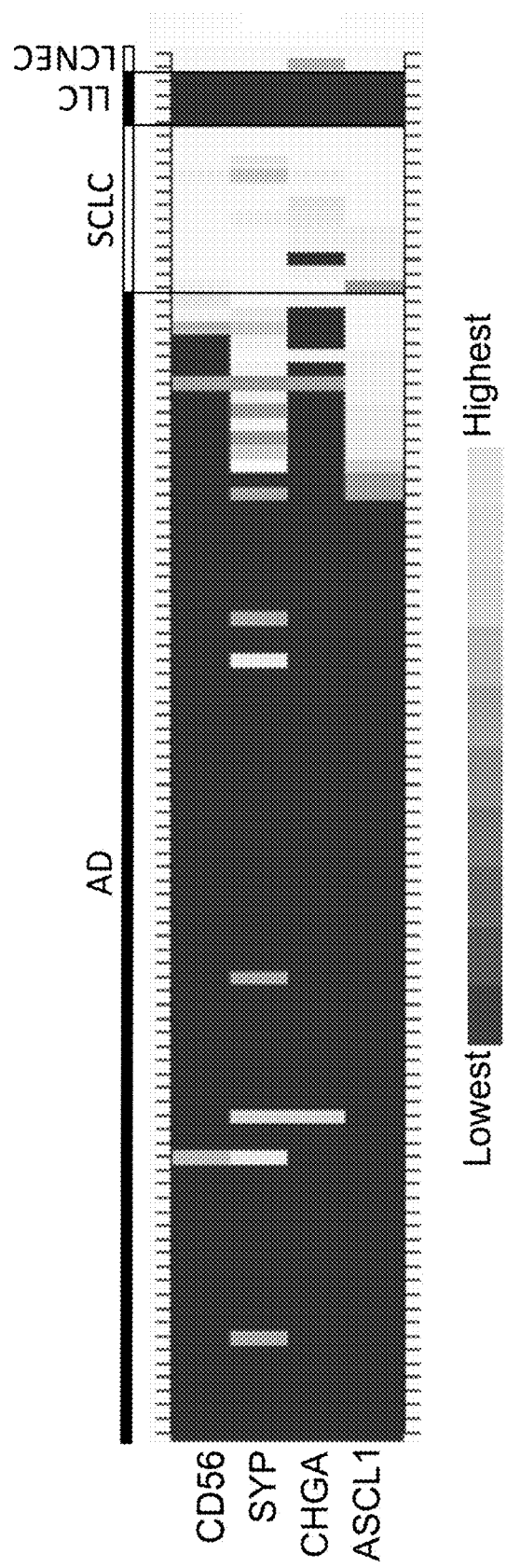

The pattern of ASCL1 immunoreactivity varied according to tumor histological subtype. In AD showing ASCL1 immunoreactivity (ASCL1+AD), ASCL1+ cells were focal and admixed with ASCL1− cells (FIGS. 3A and 3B), resulting in low to moderate LIs (Table 4). In SCLC (FIGS. 3F and 3G) and LCNEC examples (FIGS. 3K and 3L), ASCL1 immunostaining was diffuse, resulting in moderate to high LIs (Table 4). In addition, ASCL1 immunoreactivity in AD was more frequent than for CHGA (FIG. 3C) and CD56/NCAM (FIG. 3D); however, SYP (FIG. 3E) was the most common IHC NE marker expressed in this group as shown in Table 5 and illustrated in FIG. 3P. One ASCL1+ AD was not immunoreactive for any of the other IHC NE markers, whereas six ADs exhibiting reactivity for at least one of the other NE markers were ASCL1− AD (Table 6). Among SCLC (FIGS. 3H, 3I and 3J) and LCNEC (FIGS. 3M, 3N and 3O), all cases were immunoreactive for ASCL1 as well as for most other IHC NE markers (CHGA, SYP, and CD56/NCAM); whereas the remaining 4 LCC examples were not immunoreactive for any IHC NE marker, including ASCL1 (FIG. 3P).

TABLE 5

Detailed results of correlation between ASLC1 and other NE markers in all lung cancer subtypes

| SUB-TYPE | | CHGA+ | CHGA− | SYP+ | SYP− | CD56/NCAM+ | CD56/NCAM− |
|---|---|---|---|---|---|---|---|
| AD (n = 83) | No | 4 | 79 | 20 | 63 | 5 | 78 |
| | ASCL1+ (n = 15) | 3 | 12 | 14 | 1 | 4 | 11 |
| | ASCL1− (n = 68) | 1 | 67 | 6 | 62 | 1 | 67 |
| SCLC (n = 12) | No | 11 | 1 | 12 | 0 | 12 | 0 |
| | ASCL1+ (n = 12) | 11 | 1 | 12 | 0 | 12 | 0 |
| | ASCL1− (n = 0) | 0 | 0 | 0 | 0 | 0 | 0 |
| LCNEC (n = 2) | No | 2 | 0 | 2 | 0 | 2 | 0 |
| | ASCL1+ (n = 2) | 2 | 0 | 2 | 0 | 2 | 0 |

TABLE 5-continued

Detailed results of correlation between ASLC1 and other NE markers in all lung cancer subtypes

| SUB-TYPE | | CHGA+ | CHGA− | SYP+ | SYP− | CD56/NCAM+ | CD56/NCAM− |
|---|---|---|---|---|---|---|---|
| | ASCL1− (n = 0) | 0 | 0 | 0 | 0 | 0 | 0 |
| LCC (n = 4) | No | 0 | 4 | 0 | 4 | 0 | 4 |
| | ASCL1+ (n = 0) | 0 | 0 | 0 | 0 | 0 | 0 |
| | ASCL1− (n = 4) | 0 | 4 | 0 | 4 | 0 | 4 |

TABLE 6

Correlation of ASCL1 with other NE markers in AD

| AD SUBTYPE | CHGA/SYP/CD56*+ | CHGA/SYP/CD56*− |
|---|---|---|
| ASCL1+ AD (n = 15) | 14 (94%) | 1 (6%) |
| ASCL1− AD (n = 68) | 6 (9%) | 62 (91%) |

ASCL1 mRNA Expression is More Prevalent in AD than in SQCC

Figure 4:
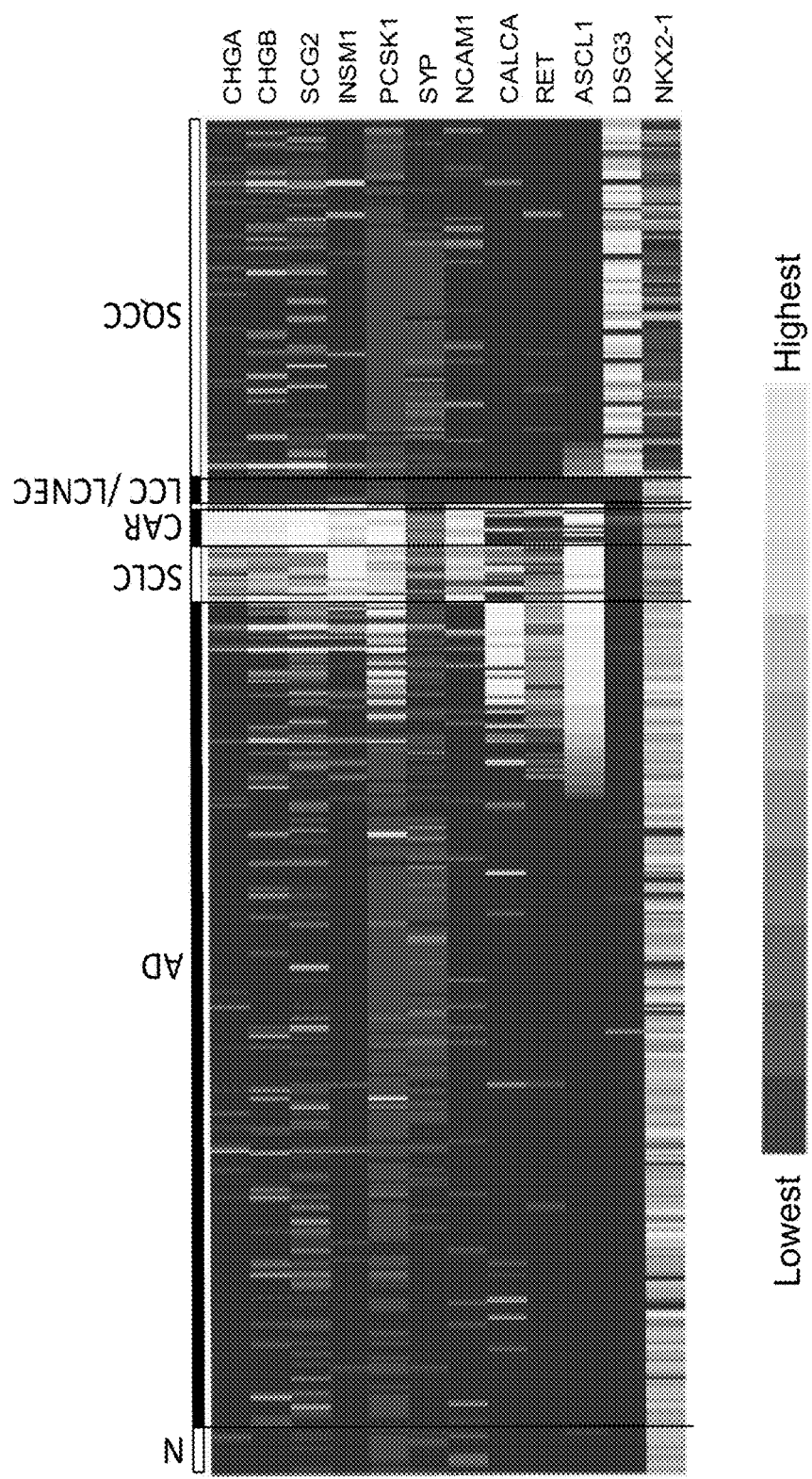
FIG. 4 is a heat map of the microarray $Log_2$ expression values using known NE genes and RET. The map also includes SQCC and AD specific genes (DSG3 and NKX2.1, respectively). ASCL1 expression is much more frequent in AD than in SQCC. Each gene is represented by the most variable probeset with the highest standard deviation.

The expression of ASCL1 and other known NE markers in Dataset 1 (FIG. 1) consisting of AD (n=232), SQCC (n=100), SCLC (n=15), adjacent non-neoplastic lung (N, n=12), and LCC and LCNEC (n=9) is shown as a heatmap in FIG. 4. The heatmap also includes the SQCC and AD differentiation genes DSG3 and NKX2.1/TTF1, respectively, and RET. ASCL1 had the highest correlation with calcitonin (CPRG/CALCA) (correlation coefficient=0.65). However, in general, there was not a high correlation between the mRNA expression levels of the NE markers (Table 7). Most NE markers had similar frequency of expression in the AD and SQCC samples. In contrast, ASCL1 was much more specific to AD than to SQCC. For a quantitative analysis, a threshold was selected for ASCL1 that corresponded to a positive IHC stain (FIG. 2). Microarray signal intensity levels above this threshold had excellent correlation with the IHC staining (correlation coefficient=0.89, FIG. 2). In AD, 44 of 232 cases (19.0%) were ASCL1+. On the other hand, in 100 SQCC only 1 of 100 cases (1.0%) was ASCL1+. Of the nine LCC, two had strong expression of ASCL1 and all other NE markers and were classified as LCNEC. Importantly, ASCL1 also was highly prevalent in other NE lung tumors, including SCLC and carcinoid tumors (CT). Six of 10 (60%) and 14 of 15 (93%) CT and SCLC, respectively, were ASCL1+.

TABLE 7

Correlation between any two NE markers in AD and SQCC that express either or both markers.

| | CHGA | CHGB | SCG2 | INSM1 | PCSK1 | SYP | NCAM1 | ASCL1 | CALCA |
|---|---|---|---|---|---|---|---|---|---|
| CHGA | 1 | | | | | | | | |
| CHGB | 0.219 | 1 | | | | | | | |
| SCG2 | 0.395 | 0.207 | 1 | | | | | | |
| INSM1 | NS* | 0.259 | 0.439 | 1 | | | | | |
| PCSK1 | NS* | 0.3 | 0.33 | 0.308 | 1 | | | | |
| SYP | NS* | NS* | NS* | NS* | NS* | 1 | | | |
| NCAM1 | NS* | NS* | NS* | NS* | NS* | NS* | 1 | | |
| ASCL1 | NS* | NS* | NS* | NS* | 0.497 | NS* | NS* | 1 | |
| CALCA | NS* | NS* | 0.177 | NS* | 0.593 | NS* | NS* | 0.65 | 1 |

*NS: Pearson correlation p-value > 0.05

Neuroendocrine Differentiation is Rare in Non-Smoker Adenocarcinomas

Figure 5:
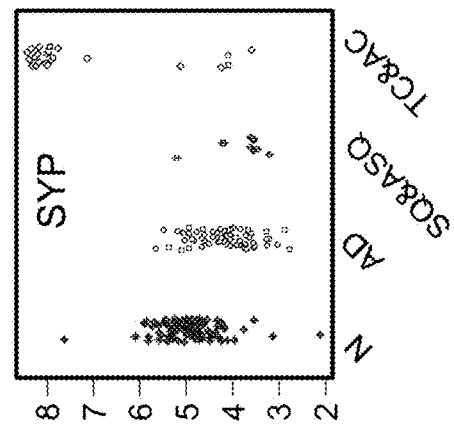
FIG. 5 contains graphs demonstrating that NE differentiation in never smoker AD is rare. In contrast with typical carcinoid (CT), no subset of AD has a distinguishably higher expression of the NE markers than non-neoplastic lung. Similar observations can be made about SQCC, but the number of samples is small.
Figure 5:
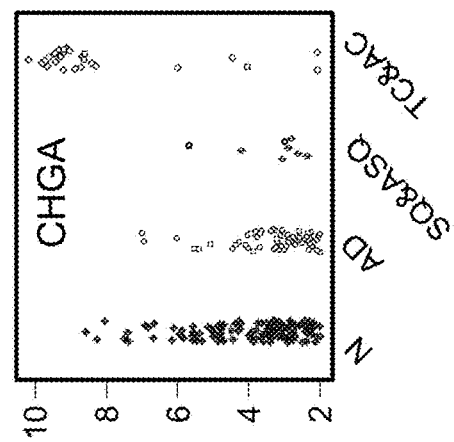
Figure 5:
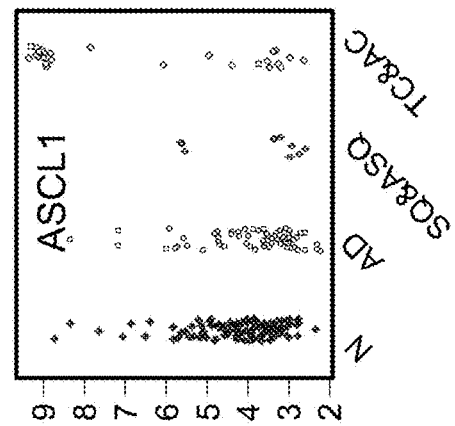
Figure 5:
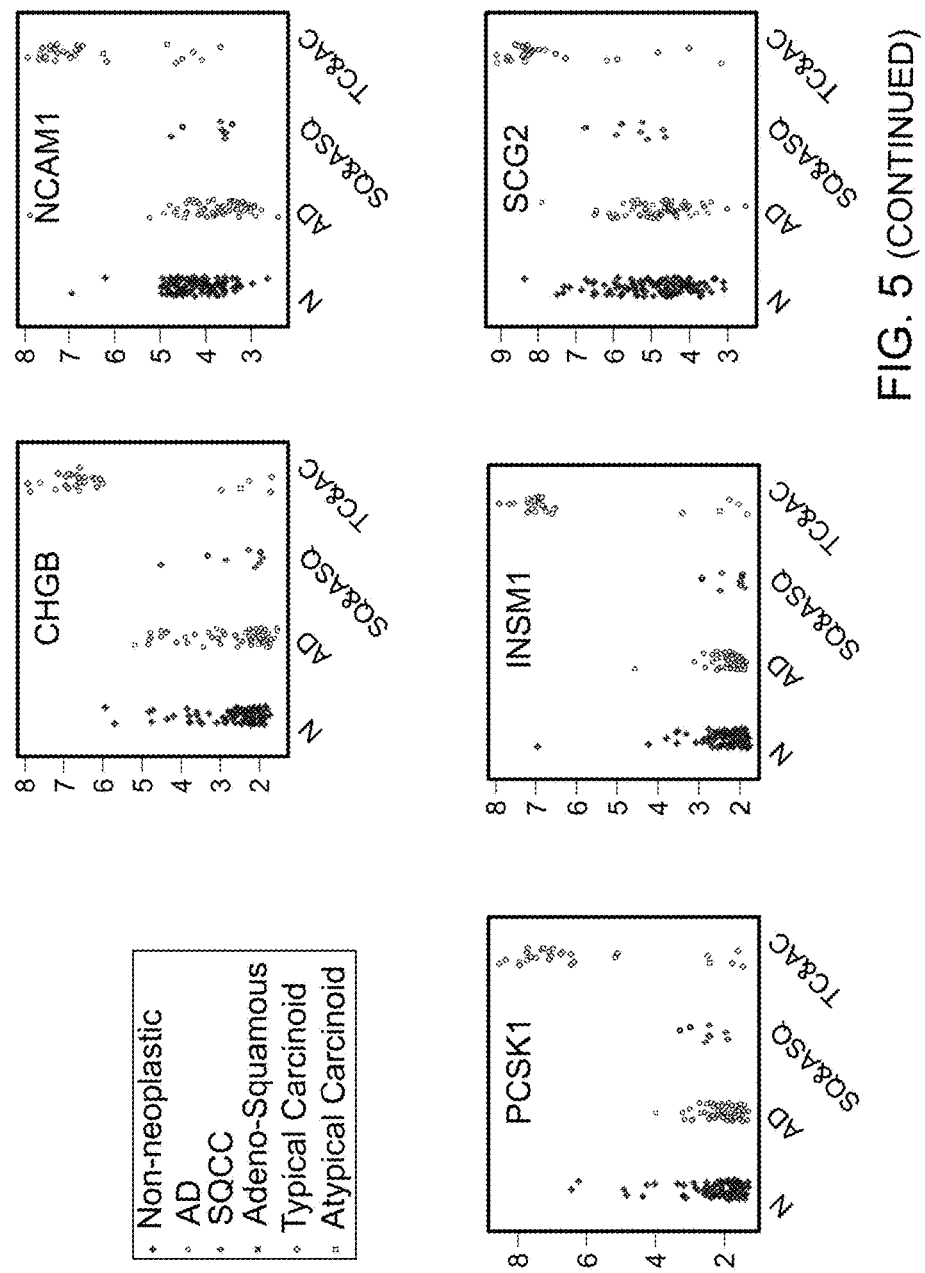

Expression levels of known NE markers were examined in the Mayo Clinic lung cancer samples from NS, which included 75 AD, 32 CT, 8 adenosquamous carcinomas and SQCC, and 125 adjacent non-neoplastic (N) samples. Compared with N, all NE markers were over-expressed in a majority of CT as expected (FIG. 5). In contrast, the expression levels of NE markers in AD were within the range of N. A subset of AD was not identified with marked over-expression of any of the NE markers. These data suggest that NE differentiation in lung AD is largely restricted to smokers.

Survival Analysis of Lung AD in Relation to ASCL1 mRNA Expression

Figure 6:
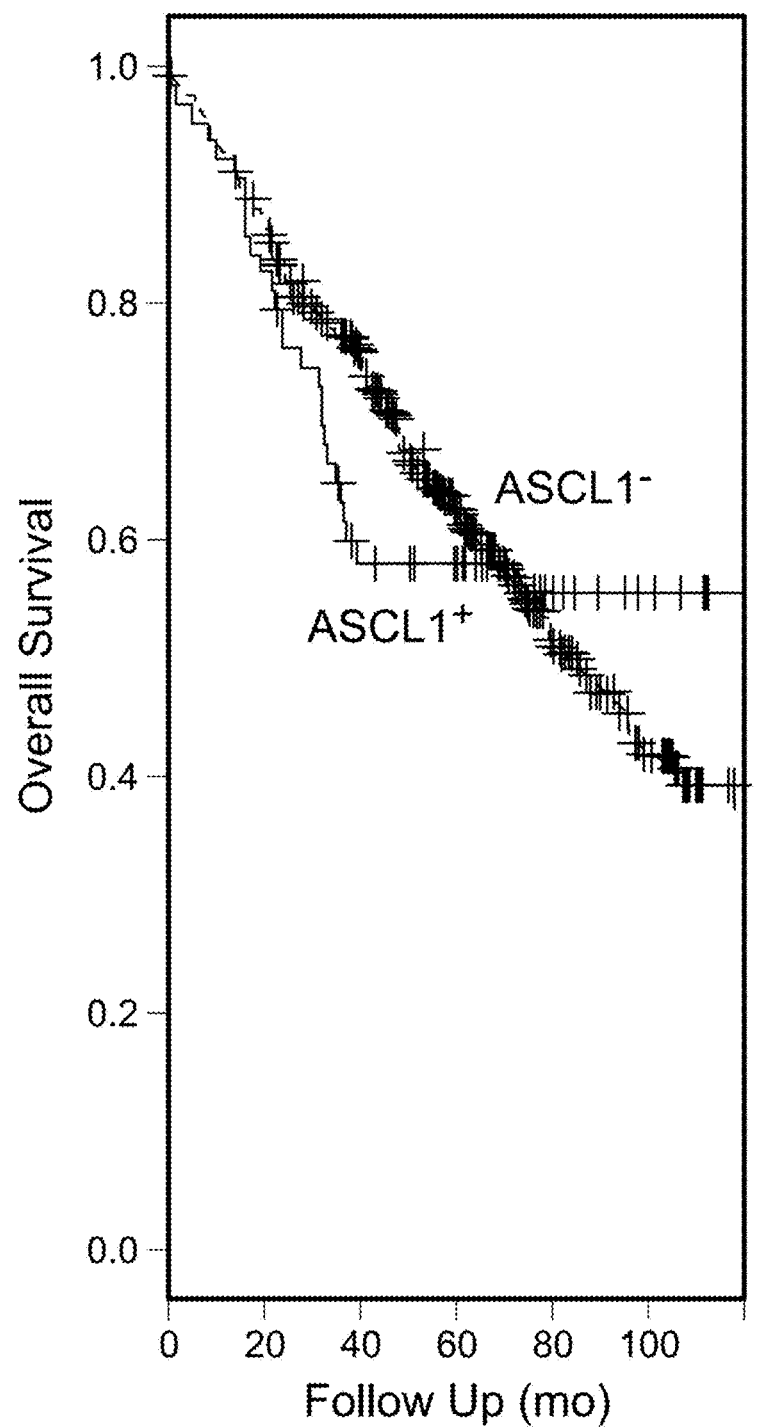
FIG. 6 is a graph of a KM plot of stage I AD in Dataset 2 based on ASCL1 status. The drop off for the ASCL1$^+$ tumors is sharper than the ASCL1$^-$ tumors, suggesting nonproportional hazard.

Given that ASCL1 is expressed in about 20% of AD, to obtain sufficient statistical power for survival analysis, the Mayo Clinic AD microarray data was combined with four publicly available AD datasets for which outcome data was available. An association was not identified between the ASCL1 expression status and survival or time to progression in stage I tumors nor in combined stage II-IV tumors (p≥0.28). However, the Kaplan Meir (KM) survival curves for ASCL1+ and ASCL1− stage I tumors had different drop off profiles (FIG. 6). ASCL1+ patients who died had significantly shorter survival times causing a sharp drop in the survival curve. Upon further investigation, this pattern was found to be consistent in all five data sets (Table 8). In the combined datasets, ASCL1+ patients who died had statistically shorter survival times than ASCL1− patients who died ($p<5\times10^{-6}$). This trend did not change after excluding samples suspected of LCNEC in the Director's Challenge dataset. A statistical test (cox.zph) indicated non-proportional hazards in ASCL1−/ASCL1+ tumors when censoring times of 6.5 or more years (p<0.05) were used. These observations suggested that ASCL1+ status might reflect a different underlying biology for these tumors. The roles of traditional prognostic markers such as age, gender, tumor grade, race, smoking status (former or current), tumor "T" stage, and tumor grade were assessed by cox analysis. The only significant parameters were age (p=10$^{-6}$) and gender (p=0.045). When stage I AD were stratified by ASCL1 status, differences in age and gender between the ASCL1+ and ASCL1− patients were not identified (group t-test and chi-square p ≥0.09).

TABLE 8

Survival times of patients with fatal stage I AD according to the ASCL1 status.

| Dataset | ASCL1+ | | | ASCL1− | | |
|---|---|---|---|---|---|---|
| | n | median | mean | n | median | mean |
| Mayo Clinic | 5 | 16.0 | 17.6 | 41 | 25.3 | 33.5 |
| Director Challenge | 14 | 31.9 | 29.4 | 93 | 45.8 | 50.3 |
| Bhattacharjee et al. | 4 | 20.3 | 20.0 | 27 | 25.5 | 31.5 |
| Kune et al. | 3 | 21.9 | 23.3 | 7 | 31.2 | 26.5 |
| Hou et al. | 1 | 4.9 | 4.9 | 11 | 24.2 | 38.4 |
| All sets | 27 | 23.6 | 24.3 | 179 | 38.2 | 41.9 |

RET mRNA Expression in ASCL1+ AD is Predictive of Overall Survival

Figure 7A:
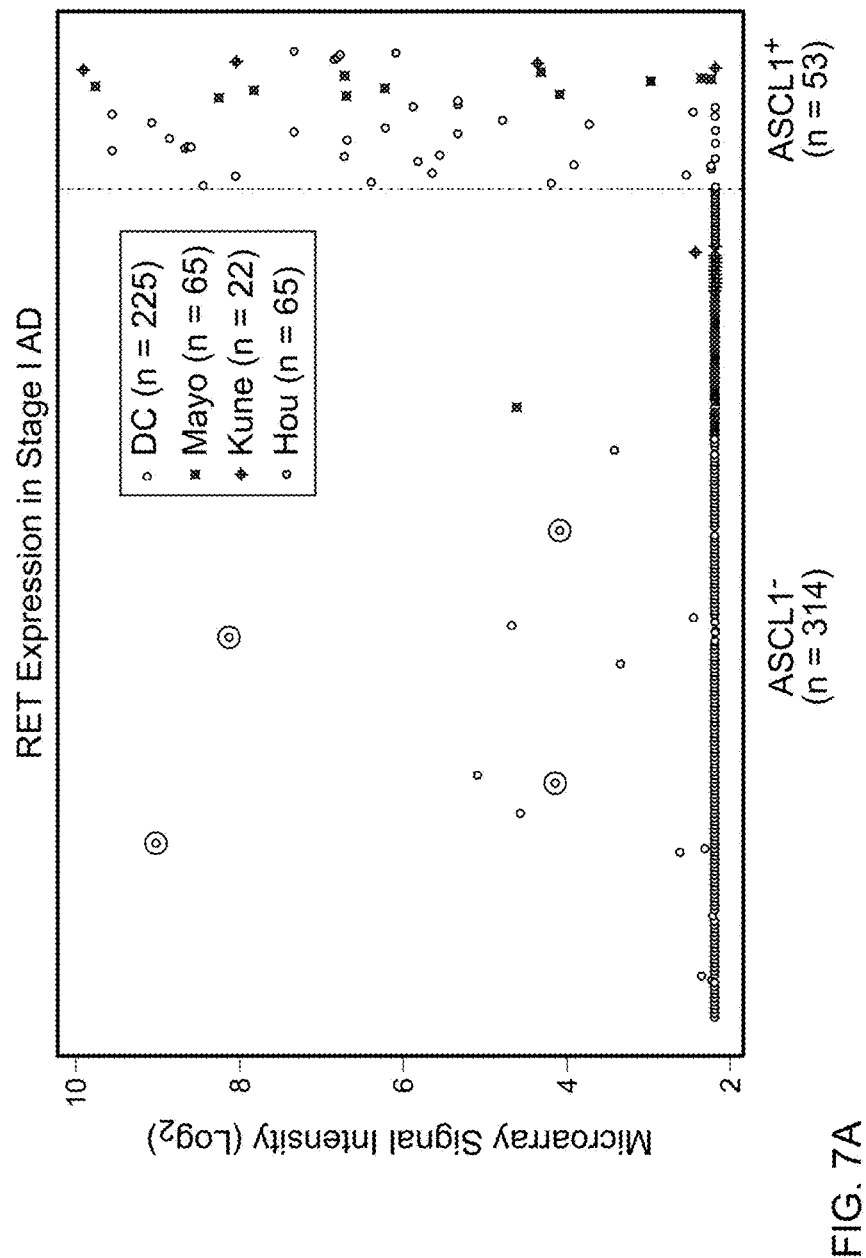
FIGS. 7A and 7B are graphs demonstrating the over representation of tumors expressing RET (211421_s_at probe set) in ASCL1$^+$ compared with ASCL1$^-$ in (A) stage I ADs (Dataset 2), and in (B) all lung cancers (Dataset 1). This over-representation was consistent in all datasets. Few samples (shown in black circles) expressed RET while ASCL1 was below noise level (arbitrary $Log_2$ signal intensity of 3.5). Data points correspond to the samples from the Mayo Clinic unless stated in the figure legends.

To gain further insight into the biology of ASCL1+ tumors, gene expression data for ASCL1+ and ASCL1− tumors were compared. Gene expression analysis used Dataset 2 (FIG. 1), which was a compendium of four sets of microarray data with follow up information and more than 22,000 common Affymetrix probesets from 593 AD including 367 stage I AD. Genes (probesets) over-expressed in ASCL1+ compared with ASCL1− tumors were identified by signal to noise ratio (SNR). The top 12 genes (16 probesets) following ASCL1 are listed in Table 9. All genes in the list were significantly over-expressed in ASCL1+ tumors after correcting for multiple comparisons (q-value<10$^{-6}$) (Storey and Tibshirani, *Proc. Natl. Acad. Sci. USA*, 100(16):9440-5 (2003)). RET was the fourth most over-expressed gene after ASCL1 followed by CALCA and C1orf95 (Table 9). FIG. 7A illustrates the expression of RET in ASCL1− and ASCL1+ stage I AD. The over-expression of RET in ASCL1+ tumors was consistent in all four datasets (FIG. 7A). RET expression was more consistent with ASCL1 than other NE markers (FIG. 4). Depending on the microarray signal threshold for calling a transcript present (Log$_2$ signal intensity of 3.5 or 4.5), 91 to 95% of samples that expressed RET also expressed ASCL1. In contrast, only 0% to 55% of samples that expressed RET also expressed CHGA, CHGB, SCG2, SYP, INSM1, PCSK1, or NCAM1. Also noted was a small portion of samples with high levels of RET in the absence of ASCL1 (black circles in FIG. 7A), indicating that in rare cases RET is expressed independent of ASCL1.

TABLE 9

Probesets (20) with highest signal to noise ratio (SNR) in ASCL1+ compared with ASCL1− tumors in Dataset 2.

| Affy Probeset | Symbol | SNR | q-value | Drug |
|---|---|---|---|---|
| 209988_s_at | ASCL1 | 2.78 | 1.4E−39 | |
| 209987_s_at | ASCL1 | 2.70 | 7.5E−27 | |
| 213768_s_at | ASCL1 | 1.51 | 4.5E−15 | |
| 217561_at | CALCA | 1.40 | 1.2E−15 | |
| 210728_s_at | CALCA | 1.33 | 4.5E−15 | |
| 210727_at | CALCA | 1.32 | 5.0E−15 | |
| 217495_x_at | CALCA | 1.16 | 4.4E−11 | |
| 209985_s_at | ASCL1 | 1.15 | 7.0E−11 | |
| 213925_at | C1orf95 | 1.09 | 9.1E−13 | |
| 211421_s_at | RET | 1.06 | 1.4E−10 | sunitinib, vandetanib |
| 205549_at | PCP4 | 1.05 | 6.5E−20 | |
| 220782_x_at | KLK12 | 1.03 | 3.2E−11 | |
| 209617_s_at | CTNND2 | 0.97 | 3.2E−11 | |
| 214023_x_at | TUBB2B | 0.93 | 1.2E−15 | brentuximab vedotin, cabazitaxel |
| 205305_at | FGL1 | 0.91 | 2.7E−13 | |
| 204623_at | TFF3 | 0.85 | 4.8E−18 | |
| 214058_at | MYCL1 | 0.85 | 7.0E−11 | |
| 205879_x_at | RET | 0.82 | 5.6E−08 | sunitinib, vandetanib |
| 210432_s_at | SCN3A | 0.80 | 3.1E−07 | riluzole |
| 209228_x_at | TUSC3 | 0.77 | 1.3E−13 | |

RET Expression Coinciding with ASCL1 was not Limited to Stage I AD

Figure 7B:
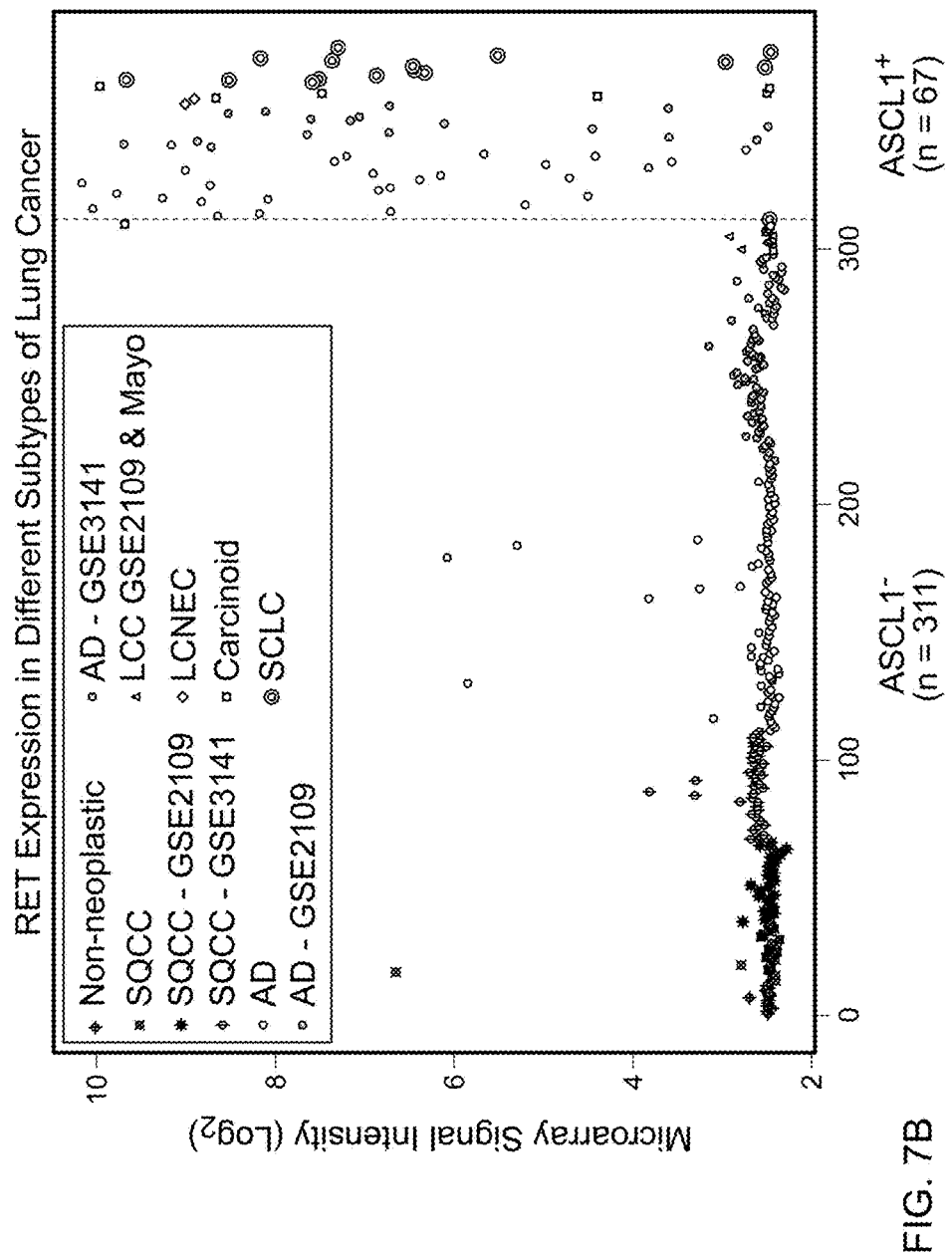

A similar ASCL1/RET co-expression was observed in all stages of AD and other lung cancer subtypes. FIG. 7B illustrates the expression of RET in Dataset 1. In SQCC where ASCL1 was largely absent, RET was also rarely expressed. In SCLC, CT, and LCC, RET expression was largely restricted to ASCL1+ tumors.

As in FIG. 7A, RET mRNA was detectable in a limited number of lung cancers that did not express ASCL1 (black circles in FIG. 7B).

Figure 8B:
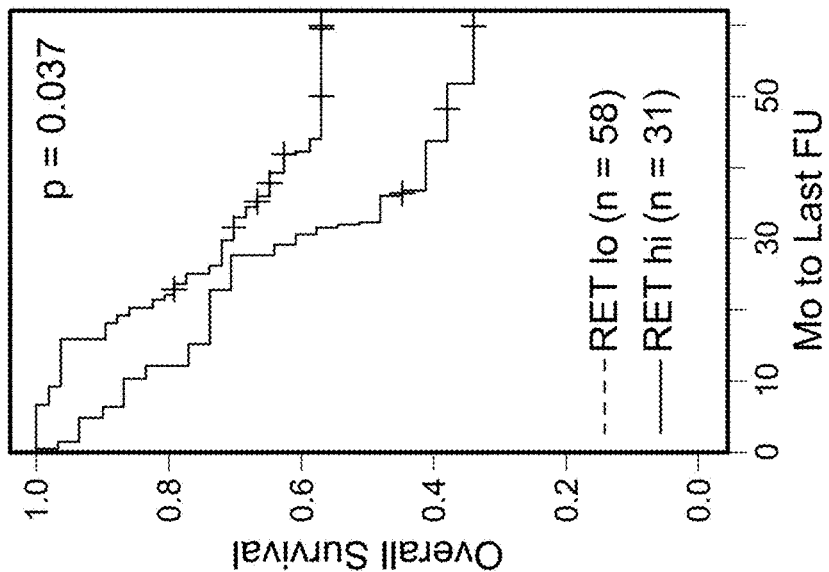
FIGS. 8A and 8B are graphs plotting overall survival in ASCL1$^+$ stage I (A) and all (B) AD as a function of the RET mRNA expression level by microarrays.
Figure 8A:
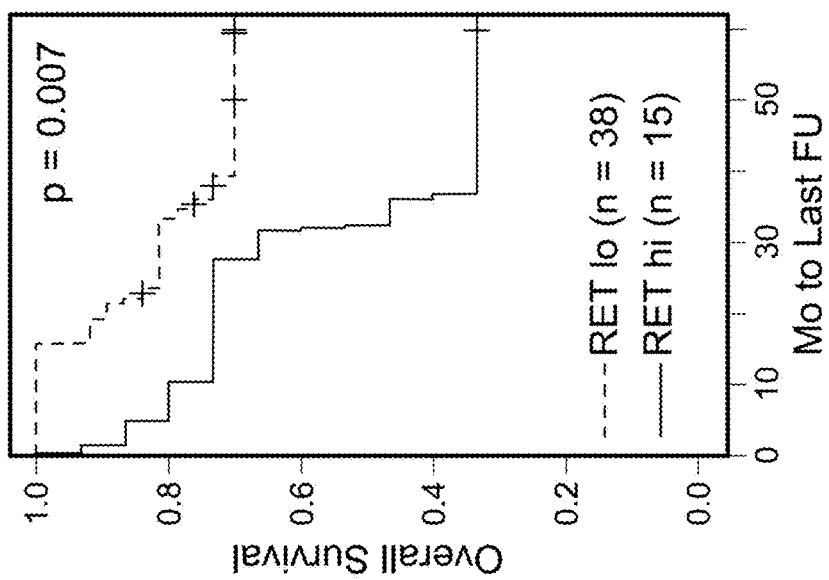

Two probesets corresponding to RET were significant in predicting the overall survival (OS) in stage I ASCL1+ tumors by cox analysis (p values of 0.029 and 0.006). High expression of RET was associated with shorter survival. In contrast, an association was not identified between the OS and RET expression level in ASCL1− tumors. For illustration, a threshold for 'low' and 'high' expression of RET in a Kaplan Meir (KM) plot was selected as shown in FIG. 8A. The results did not appreciably change after excluding samples where an alternative diagnosis of LCNEC was possible. Using the same threshold, RET mRNA also was significant in predicting OS in all AD (FIG. 8B).

RET Protein Expression Analysis by IHC

Figure 9B:
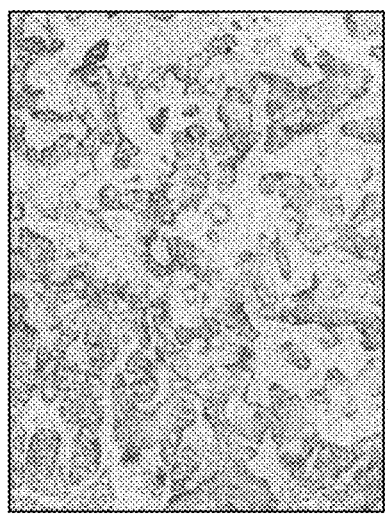
FIGS. 9A-E contain photographs and graphs of RET protein expression by IHC. RET staining in fatal adenocarcinoma was typically much less intense in ASCL1$^-$ (A) than in ASCL1$^+$ (B) tumors. (C) Co-IHC of ASCL1 (nuclear brown staining) and RET (cytoplasmic red staining) identified areas with overlapping expression of the two proteins. (D) KM plot of 14 ASCL1$^+$ AD samples indicate a significant association with OS (p=0.05). (E) When samples were not stratified by the ASCL1 expression, RET IHC was not significant in predicting OS (overall survival).
Figure 9C:
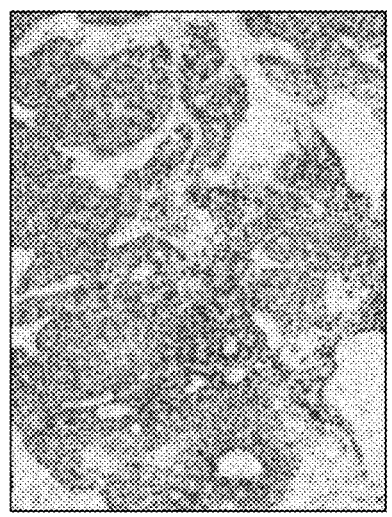
Figure 9A:
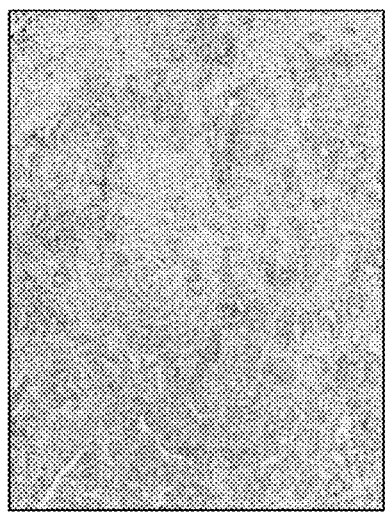

A select set of Mayo AD samples with expression data by the microarrays were immunostained for RET. RET protein expression by IHC was more prevalent than expected from the microarrays, perhaps due to the sensitivity of antibody to multiple variants of RET. A blush staining was observed in some ASCL1− cases with RET mRNA expression below detection levels by microarrays (FIG. 9A). However, ASCL1+ cases from fatal tumors often had intensely stained areas (FIG. 9B). There was a significant correlation between RET IHC scores and microarray signal intensity by the RET probeset used in OS analysis (rho=0.43, p<0.02). An ASCL1/RET co-IHC assay was developed, and overlapping tumor areas with positive staining for both proteins were frequently found (FIG. 9C). However, because of the discrepancies in sensitivity and specificity of RET and ASCL1 antibodies or because of ASCL1 independent activation of RET, areas with positive RET staining without ASCL1 expression also were encountered.

Figure 9E:
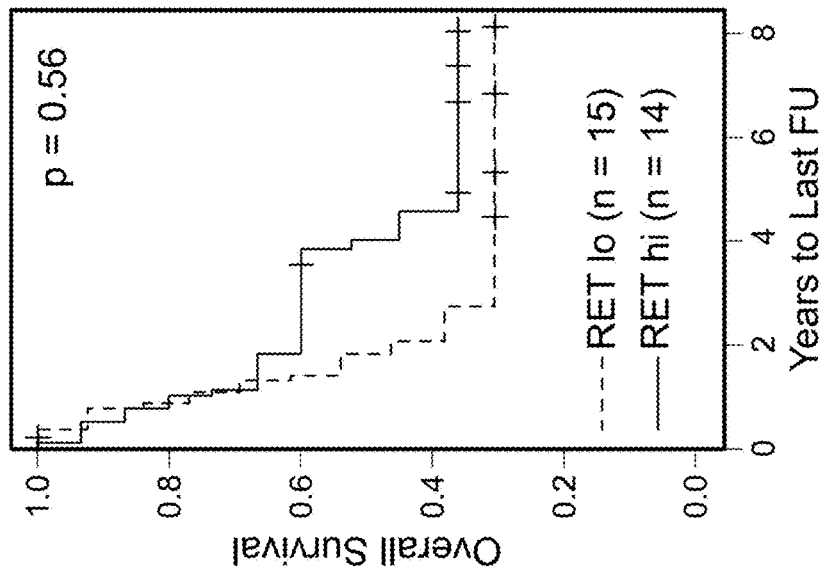
Figure 9D:
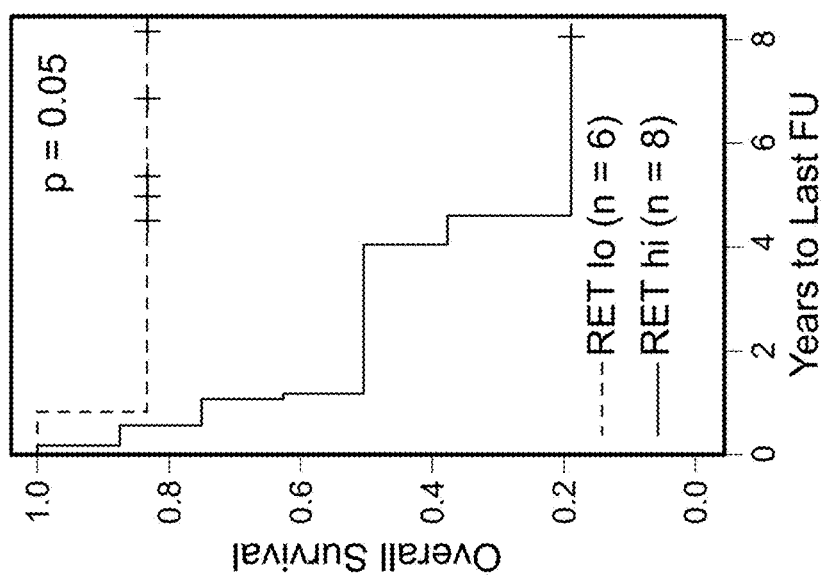
Figure 10:
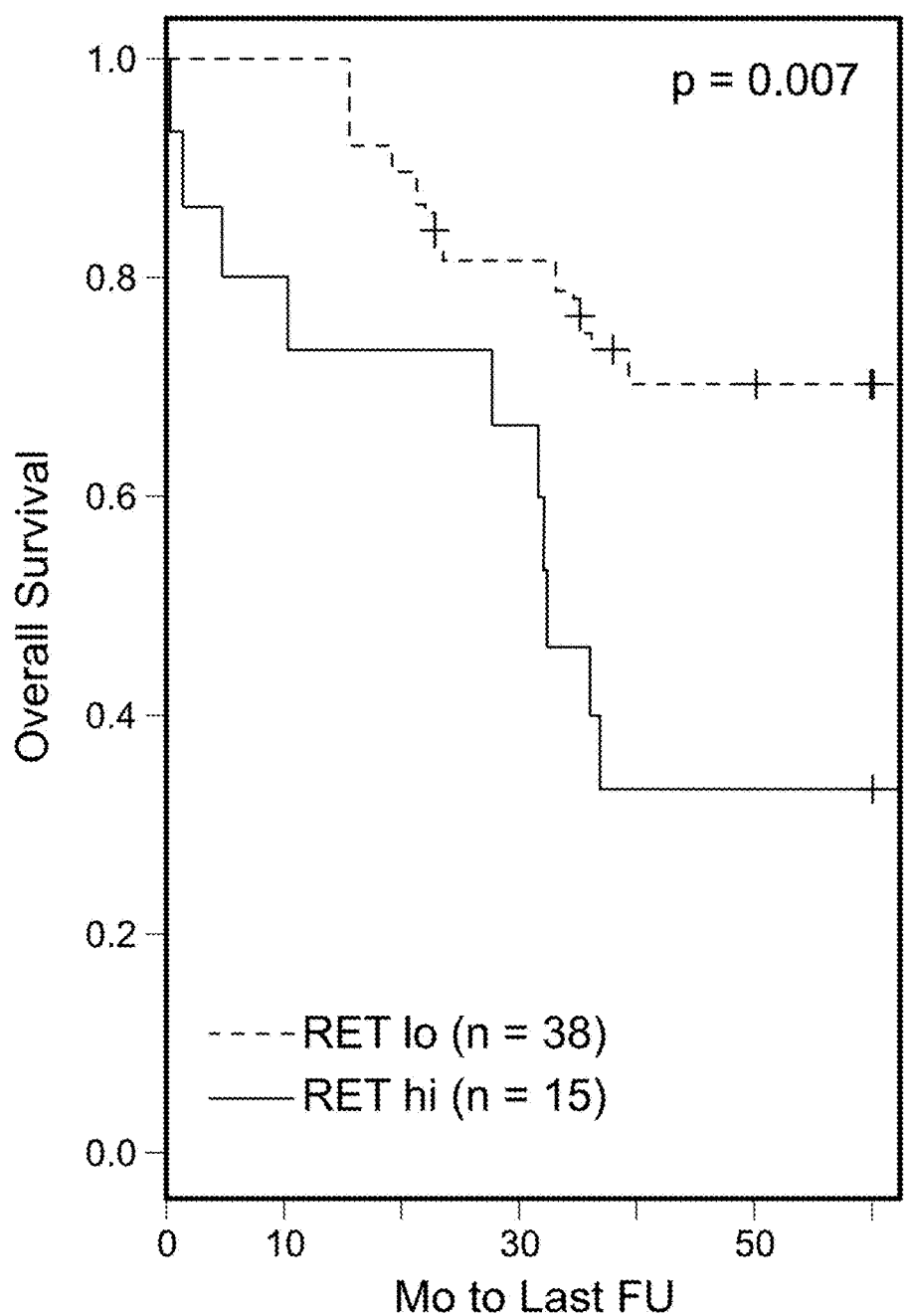
FIG. 10 is a Kaplan Meir plot of the overall survival (OS) in ASCL1$^+$ stage I AD in patients with low (n=38) and high (n=15) expression levels of RET. A significant association with the overall survival was identified (p=0.007).
Figure 11:
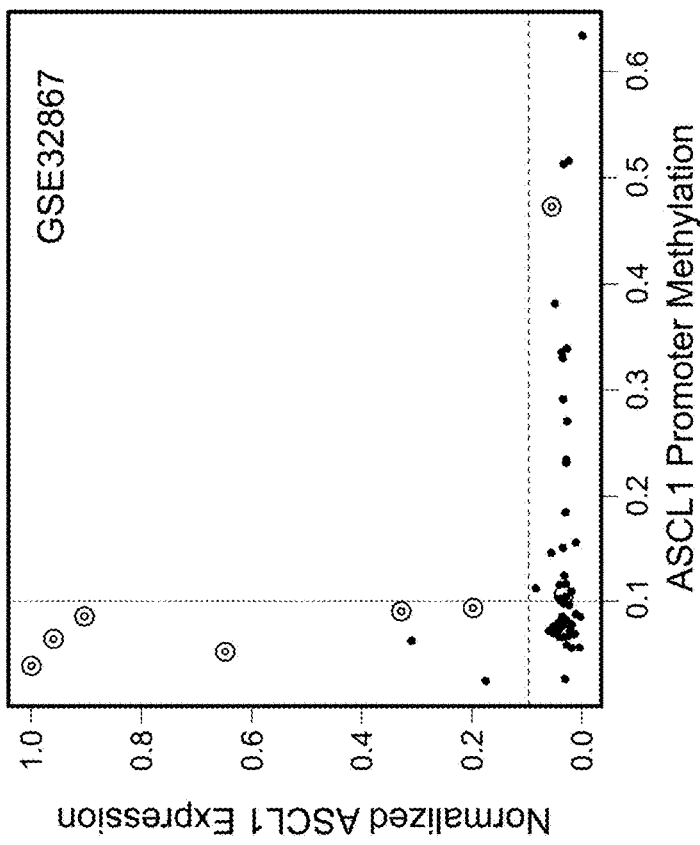
FIG. 11 is a plot of ASCL1 and RET expression versus promoter methylation of the ASCL1 promoter in the GSE32867 dataset. This data indicates that promoter hypomethylation increases expression levels of the ASCL1 transcript. Interestingly, high expression level of ASCL1 is significantly associated with high level of RET. In the plot, samples with high transcript levels of RET are indicated by circles around the solid circles. RET and ASCL1 expression levels are based on the Illumina ILMN_1655610 and ILMN_1701653 probesets, respectively. ASCL1 promoter methylation is assessed by the cg20053158 probeset. High RET expression is marked by circles.
Figure 12:
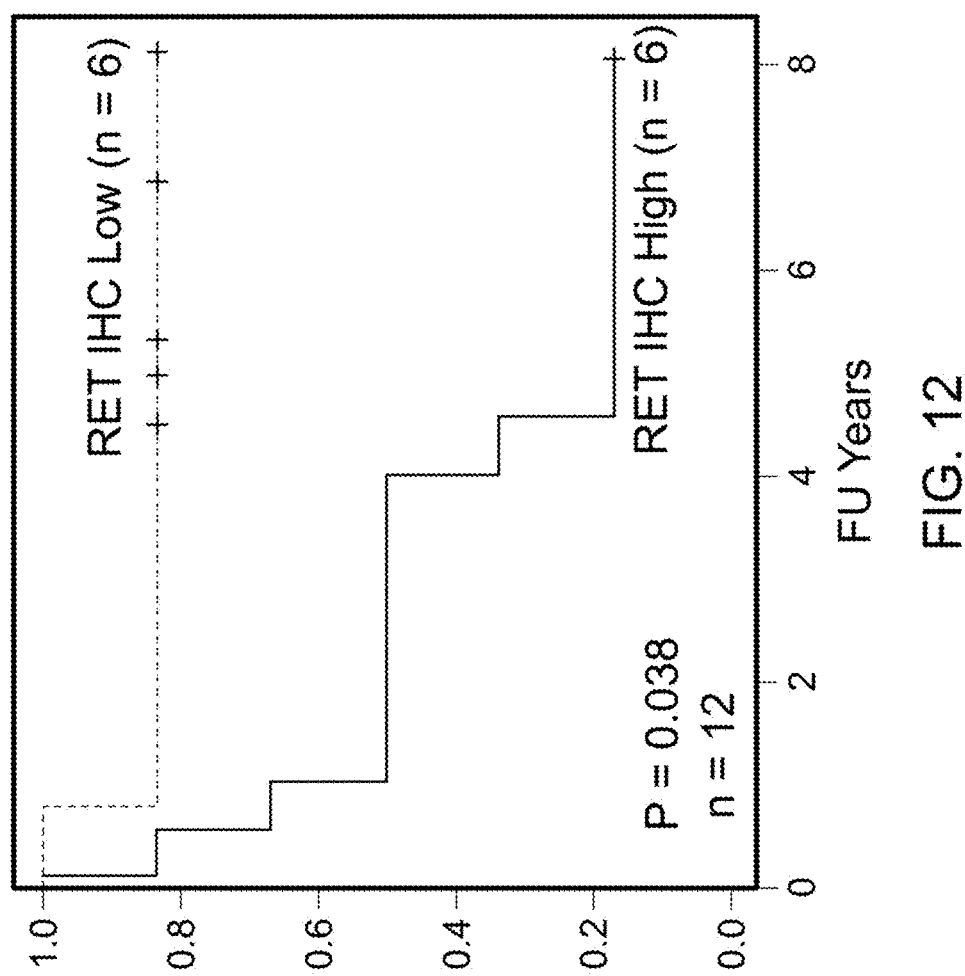
FIG. 12 is a Kaplan Meir plot of the ASCL1$^+$ AD patients overall survival based on the levels of the RET protein by IHC. Samples are from Mayo patients and were used in the discovery step by microarrays. A significant association between RET IHC and the overall survival was identified (p=0.038).

RET protein level by IHC was predictive of OS in the Mayo AD samples, which also were positive for ASCL1 by IHC (log-rank test p value=0.05, FIG. 9D). When cases were not stratified by the ASCL1 expression, RET IHC was not predictive of OS (FIG. 9E). In this situation, median survival times of tumors with 'low' levels of RET was slightly less than tumors with 'high' levels of RET, but this difference was statistically insignificant. These results indicate that RET protein is predictive of OS survival only in the context of ASCL1 expression.

Gene Set Analysis of ASCL1+ Tumors

To gain further insight in the biology of ASCL1+ tumors, gene set enrichment analysis was performed by the GSA program and MSigDB version 3 with close to 7000 gene sets. The results are shown in Table 10. Notably, positively and negatively associated gene sets included OSADA_ASCL1_TARGETS_UP and _DN, respectively. These sets contained genes that were up and down regulated by ASCL1 in a study of ASCL1-transduced A549 lung AD cells (Osada et al., *Cancer Res.*, 68(6):1647-55 (2008)). Importantly, RET was among the target genes up regulated by ASCL1 in the OSADA_ASCL1_TARGETS_UP set corroborating the observations in patient data. In the module corresponding to human chromosome and cytogenetic bands, 12q22 and 8p22 were enriched. Ten of 37 genes (including ASCL1) on chr12q22 and twelve of 41 genes on chr 8p22 were significantly over-expressed in ASCL1+ tumors. The high concentration of over-expressed genes in these regions suggested potential copy number changes.

TABLE 10

Gene sets positively and negatively associated with ASCL1+ compared with ASCL1− stage I tumors.

| Pathway Names | Frequency | Score |
|---|---|---|
| Positive Associations | | |
| TATCTGG, MIR-488 | 100 | 0.76 |
| BONE_REMODELING | 90 | 1.2 |
| TISSUE_REMODELING | 85 | 1.16 |
| module_382 | 85 | 2.46 |
| chr12q22 | 85 | 1.64 |
| OSADA_ASCL1_TARGETS_UP | 80 | 1.16 |
| chr8p22 | 80 | 1.72 |
| HANN_RESISTANCE_TO_BCL2_INHIBITOR_DN | 80 | 0.95 |
| Negative Associations | | |
| CHARAFE_BREAST_CANCER_LUMINAL_VS_BASAL_DN | 100 | −0.85 |
| HUANG_DASATINIB_RESISTANCE_UP | 100 | −1.34 |
| BOYLAN_MULTIPLE_MYELOMA_D_DN | 100 | −0.92 |
| MARSON_FOXP3_TARGETS_UP | 100 | −1.06 |
| module_543 | 100 | −2.66 |
| HUMMEL_BURKITTS_LYMPHOMA_DN | 95 | −1.48 |
| WANG_BARRETTS_ESOPHAGUS_AND_ESOPHAGUS_CA | 95 | −1.34 |
| LEE_EARLY_T_LYMPHOCYTE_DN | 95 | −1.49 |
| KEGG_VIRAL_MYOCARDITIS | 95 | −1.55 |
| module_411 | 95 | −0.68 |
| FUJII_YBX1_TARGETS_UP | 90 | −1.51 |
| GNF2_RAP1B | 90 | −1.41 |
| module_223 | 90 | −0.96 |
| KEGG_CELL_ADHESION_MOLECULES_CAMS | 90 | −1.18 |
| BIOCARTA_TH1TH2_PATHWAY | 90 | −2.42 |
| module_341 | 90 | −0.65 |
| WU_CELL_MIGRATION | 85 | −0.74 |
| OSADA_ASCL1_TARGETS_DN | 80 | −1.29 |
| KIM_LRRC3B_TARGETS | 80 | −1.94 |
| CASTELLANO_NRAS_TARGETS_UP | 80 | −0.86 | mRNA correlates of aggressive behavior in stage I ASCL1+ AD also were examined. Tumors from patients who died in less than 3.5 years following surgery (n=21) and from patients who survived more than 6 years following surgery (n=20) were designated as aggressive and non-aggressive tumors, respectively. When probesets were ranked by SNR in aggressive versus non-aggressive tumors, two probesets for RET were among the list of top 10 probesets. GSA analysis in these tumors identified six gene sets (Table 11). Most notably, KANG-CISPLATIN-RESISTANCE-UP was positively associated with aggressive tumors. This set included genes that were up-regulated in gastric cancer cell lines resistant to cisplatin (Kang et al., *Clin. Cancer Res.*, 10(1 Pt 1):272-84 (2004)).

TABLE 11

Gene sets positively and negatively associated with aggressive behavior in ASCL1+ stage I AD.

| Pathway Names | Frequency | Score |
|---|---|---|
| Positive Associations | | |
| CHIANG_LIVER_CANCER_SUBCLASS_POLYSOMY7_UP | 100 | 1.39 |
| V$AP1_Q4 | 85 | 0.35 |
| module_94 | 85 | 0.4 |
| KANG_CISPLATIN_RESISTANCE_UP | 80 | 0.97 |
| ENZYME_INHIBITOR_ACTIVITY | 80 | 0.53 |
| Negative Associations | | |
| V$MAX_01 | 85 | −0.3 |

In summary, the results provided herein demonstrate that lung cancer patients can be examined for the presence of lung cancer cells expressing ASCL1 (e.g., an elevated level ASCL1) and RET (e.g., an elevated level RET). If the presence of lung cancer cells expressing ASCL1 and RET is detected in a particular lung cancer patient, then that lung cancer patient can be classified as having lung adenocarcinoma characterized by neuroendocrine differentiation and/or as having a poor survival prognosis. In some cases, lung cancer patients classified as having lung adenocarcinoma characterized by neuroendocrine differentiation can be treated as described herein.

Example 2

Genes Over Expressed in Lung Adenocarcinoma Expressing ASCL1 and RET

The genes listed in Table 12 were found to be overexpressed in lung adenocarcinoma samples that express ASCL1 and RET. Additional information about each of these ten genes is provided in Table 13. Possible drugs for treating lung adenocarcinoma characterized by neuroendocrine differentiation are listed in Table 14, Table 1, Table 2A, or Table 2B.

TABLE 12

| Symbol | Entrez Gene Name |
|---|---|
| KCNMB4 | potassium large conductance calcium-activated channel, subfamily M, beta member 4 |
| RET | ret proto-oncogene |
| SCN3A | sodium channel, voltage-gated, type III, alpha subunit |
| ADRA2A | adrenoceptor alpha 2A |
| FGA | fibrinogen alpha chain |
| FGB | fibrinogen beta chain |

TABLE 12-continued

| Symbol | Entrez Gene Name |
|---|---|
| KIT | v-kit Hardy-Zuckerman 4 feline sarcoma viral oncogene homolog |
| DDC | dopa decarboxylase (aromatic L-amino acid decarboxylase) |
| TUBB2B | tubulin, beta 2B class IIb |
| CHRNA9 | cholinergic receptor, nicotinic, alpha 9 (neuronal) |

TABLE 13

| Symbol | Affymetrix | Location | Type(s) | Entrez Gene ID for Human | Entrez Gene ID for Mouse | Entrez Gene ID for Rat |
|---|---|---|---|---|---|---|
| KCNMB4 | 219287_at | Plasma Membrane | ion channel | 27345 | 58802 | 66016 |
| RET | 205879_x_at | Plasma Membrane | kinase | 5979 | 19713 | 24716 |
| SCN3A | 210432_s_at | Plasma Membrane | ion channel | 6328 | 20269 | 497770 |
| ADRA2A | 209869_at | Plasma Membrane | G-protein coupled receptor | 150 | 11551 | 25083 |
| FGA | 205649_s_at | Extracellular Space | other | 2243 | 14161 | 361969 |
| FGB | 204988_at | Extracellular Space | other | 2244 | 110135 | 24366 |
| KIT | 205051_s_at | Plasma Membrane | kinase | 3815 | 16590 | 64030 |
| DDC | 205311_at | Cytoplasm | enzyme | 1644 | 13195 | 24311 |
| TUBB2B | 214023_x_at | Cytoplasm | other | 347733 | 73710 | 291081 |
| CHRNA9 | 221107_at | Plasma Membrane | transmembrane receptor | 55584 | 231252 | 65024 |

TABLE 14

| Symbol | Drug(s) for treating lung adenocarcinoma characterized by neuroendocrine differentiation |
|---|---|
| KCNMB4 | tedisamil |
| RET | sunitinib, vandetanib |
| SCN3A | riluzole |
| ADRA2A | paliperidone, risperidone, antazoline/naphazoline, acetaminophen/clemastine/pseudoephedrine, articaine/epinephrine, bupivacaine/epinephrine, caffeine/ergotamine, acetaminophen/dexbrompheniramine/pseudoephedrine, dapiprazole, dexbrompheniramine/pseudoephedrine, chlorpheniramine/ibuprofen/pseudoephedrine, dipivefrin, cetirizine/pseudoephedrine, asenapine, epinephrine/prilocaine, epinephrine/lidocaine, PYM-50018, V2006, lurasidone, paliperidone palmitate, fexofenadine/pseudoephedrine, guaifenesin/phenylpropanolamine, oxymetazoline, prazosin, phenylpropanolamine, ephedrine, tolazoline, guanfacine, guanabenz, guanethidine, phenoxybenzamine, dexmedetomidine, UK 14304, clonidine, dexefaroxan, quinidine, polythiazide/prazosin, chlorothiazide/methyldopa, chlorthalidone/clonidine, propafenone, guanadrel, hydrochlorothiazide/methyldopa, metaraminol, tizanidine, quetiapine, D-pseudoephedrine, apraclonidine, venlafaxine, phentolamine, labetalol, mephentermine, propylhexedrine, yohimbine, dihydroergotamine, ergotamine, norepinephrine, alpha-methyl dopa, epinephrine, dopamine, chlorpheniramine/phenylpropanolamine, desloratadine/pseudoephedrine, acrivastine/pseudoephedrine, carbinoxamine/pseudoephedrine, brompheniramine/codeine/phenylpropanolamine, pseudoephedrine/triprolidine, codeine/pseudoephedrine/triprolidine, carbetapentane/chlorpheniramine/ephedrine/phenylephrine, brompheniramine/dextromethorphan/pseudoephedrine, chlorpheniramine/hydrocodone/pseudoephedrine, azatadine/pseudoephedrine, naphazoline, carbinoxamine/dextromethorphan/pseudoephedrine |
| FGA | F2 |
| FGB | F2 |
| KIT | dasatinib, sunitinib, pazopanib, tivozanib, OSI-930, telatinib, tandutinib, imatinib, sorafenib |
| DDC | carbidopa/entacapone/levodopa, carbidopa/levodopa, S(−)-carbidopa, L-dopa |
| TUBB2B | brentuximab vedotin, cabazitaxel |
| CHRNA9 | ABT-089, isoflurane, mecamylamine, succinylcholine, rocuronium, doxacurium, amobarbital, mivacurium, pipecuronium, rapacuronium, metocurine, atracurium, cisatracurium, acetylcholine, nicotine, D-tubocurarine, arecoline, enflurane, pancuronium, vecuronium |

Example 3

Methods for Confirming Effectiveness of Drugs for Treating Lung Adenocarcinoma Characterized by Neuroendocrine Differentiation Two cell lines are used to confirm the effectiveness of drugs for treating lung adenocarcinoma characterized by neuroendocrine differentiation. The first is the HCC1833 cell line, which was derived from lung AD and has high expression levels of ASCL1 and RET. The second in the A549 cell line which has low endogenous expression of ASCL1 and is stably transfected with ASCL1 (A549-As$^+$). A549-As$^+$ captures salient features of ASCL1$^+$ lung AD from patients, including increased expression of RET. HCC1833 are stably transfected with ASCL1 siRNA to knock down ASCL1 and produce a HCC1833-AsKD cell line. Lowering ASCL1 expression leads to low levels of RET expression.

Selected drugs such as sunitinib, sorafinib, or others listed in Table 14 are incubated with A549 and A549-As$^+$ cells in vitro and HCC1833 and HCC1833-AsKD cells in vitro. The cells are treated in culture at various concentrations (e.g., 10 to 100 nM or 2 to 10 µM concentrations). The treated cell lines are examined for sensitivity to the selected drugs. Cell viability and apoptosis are assessed using standard assays to compare sensitivity of A549, A549-As$^+$, HCC1833, and HCC1833-AsKD cells to the selected drugs.

In vivo methods are performed as follows. HCC1833 or A549-As$^+$ cells are transplanted into Nude mice subcutaneously or by IP injections. Tumors are allowed to grow, and the animals are treated to receive daily treatments of a selected drug (e.g., sunitinib and/or sorafinib) given by oral administration at a particular dose (e.g., 30 mg/kg or 60 mg/kg). Tumor growth is evaluated twice-weekly by measurement of tumor volume, and histology of the tumors is assessed at the end of the treatment or after mice become moribund.

Figure 13:
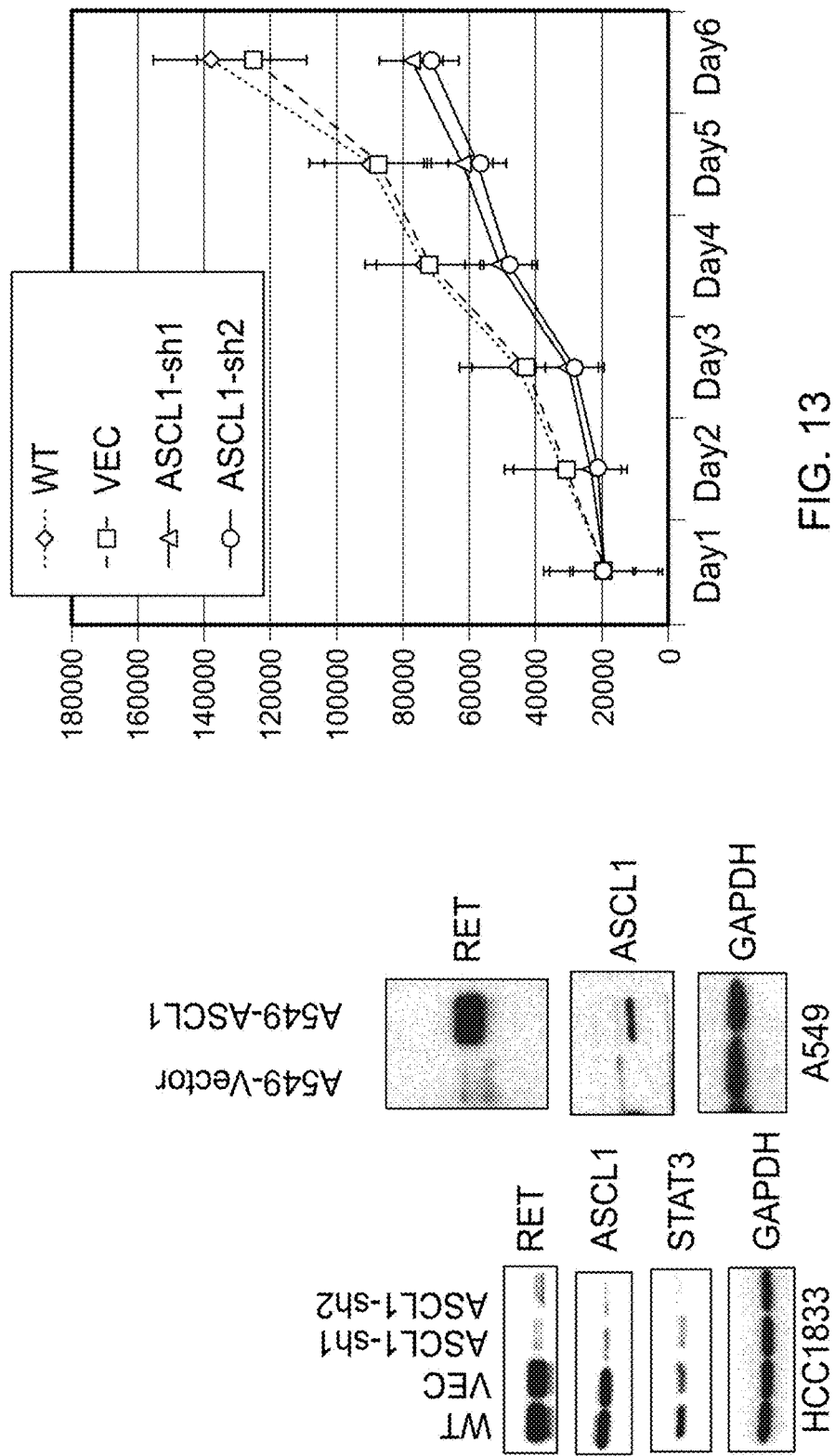
FIG. 13 contains three graphs of an in vitro analysis that confirms that ASCL1 regulates RET expression.
Figure 14:
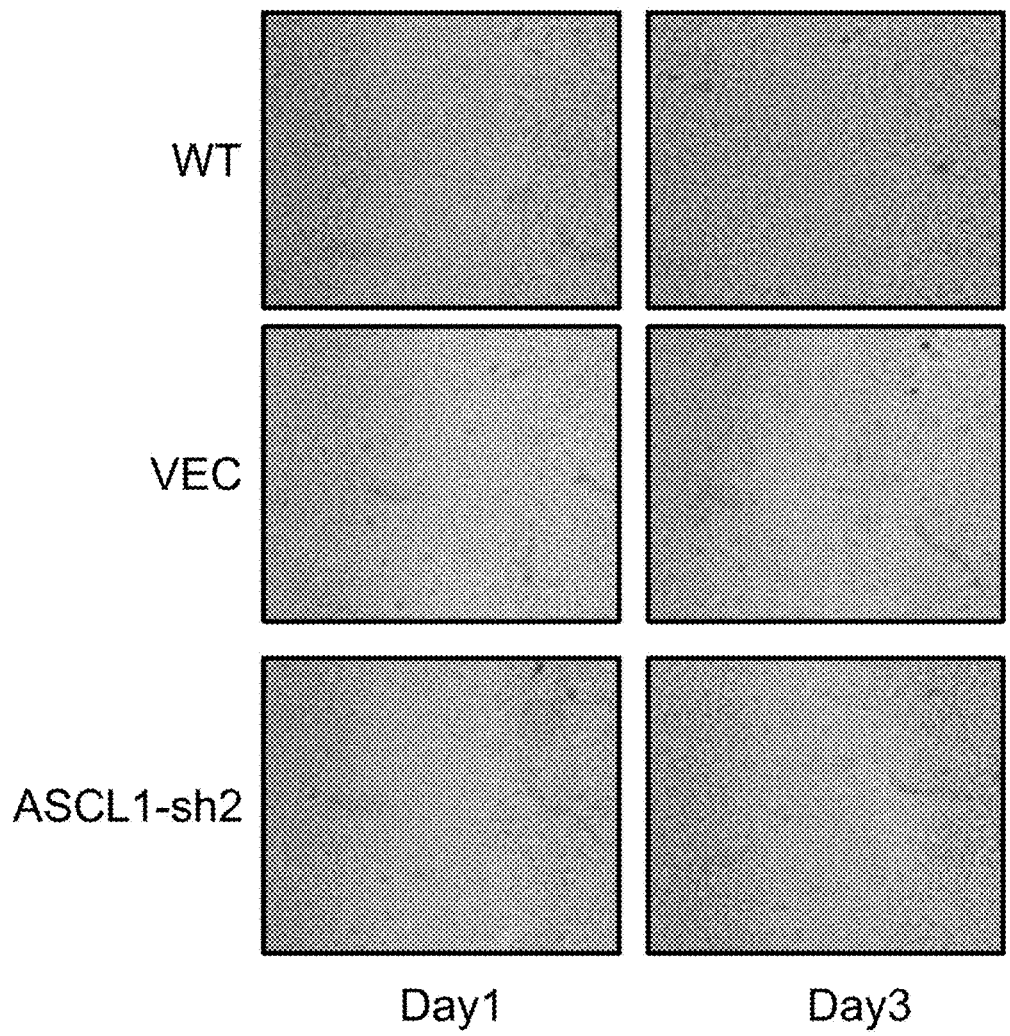
FIG. 14 contains photographs of cells from a filling the gap scratch assay (see, e.g., Liang et al., Nature Protocols, 2:329-333 (2007)). Wild-type HCC1833 cells and HCC1833 cells transfected with a control vector filled most of the gap by day 3, while HCC1833 cells transfected with an ASCL1 knock down vector (ASCL1-sh2 cells) did not fill as much of the gap, indicating that wild-type HCC1833 cells and cells transfected with empty vector (VEC) have a higher migration capacity than cells transfected with ASCL1 shRNA (ASCL1-sh2).

The HCC1833 adenocarcinoma cell line expressed high endogenous levels of ASCL1 and RET (FIG. 13, left). Transfection with sh1 (a small interfering RNA construct that includes: GCCAACAAGAAGATGAGTAAG (SEQ ID NO: 1)) or sh2 (a small interfering RNA construct that includes: CAACCGCGTCAAGTTGGTCAA (SEQ ID NO:2)) reduced ASCL1 expression as well as RET expression (FIG. 13, left). These results suggest that ASCL1 is an upstream regulator of RET. In addition, STAT3 expression (in JAK/STAT3 pathway) went down. Knocking down ASCL1 expression also caused reduced cell proliferation (FIG. 13, right). Also, HCC1833 cells with reduced ASCL1 expression (ASCL1-sh2 cells) exhibited a much slower ability to filling the gap in a scratch assay (FIG. 14).

Figure 15:
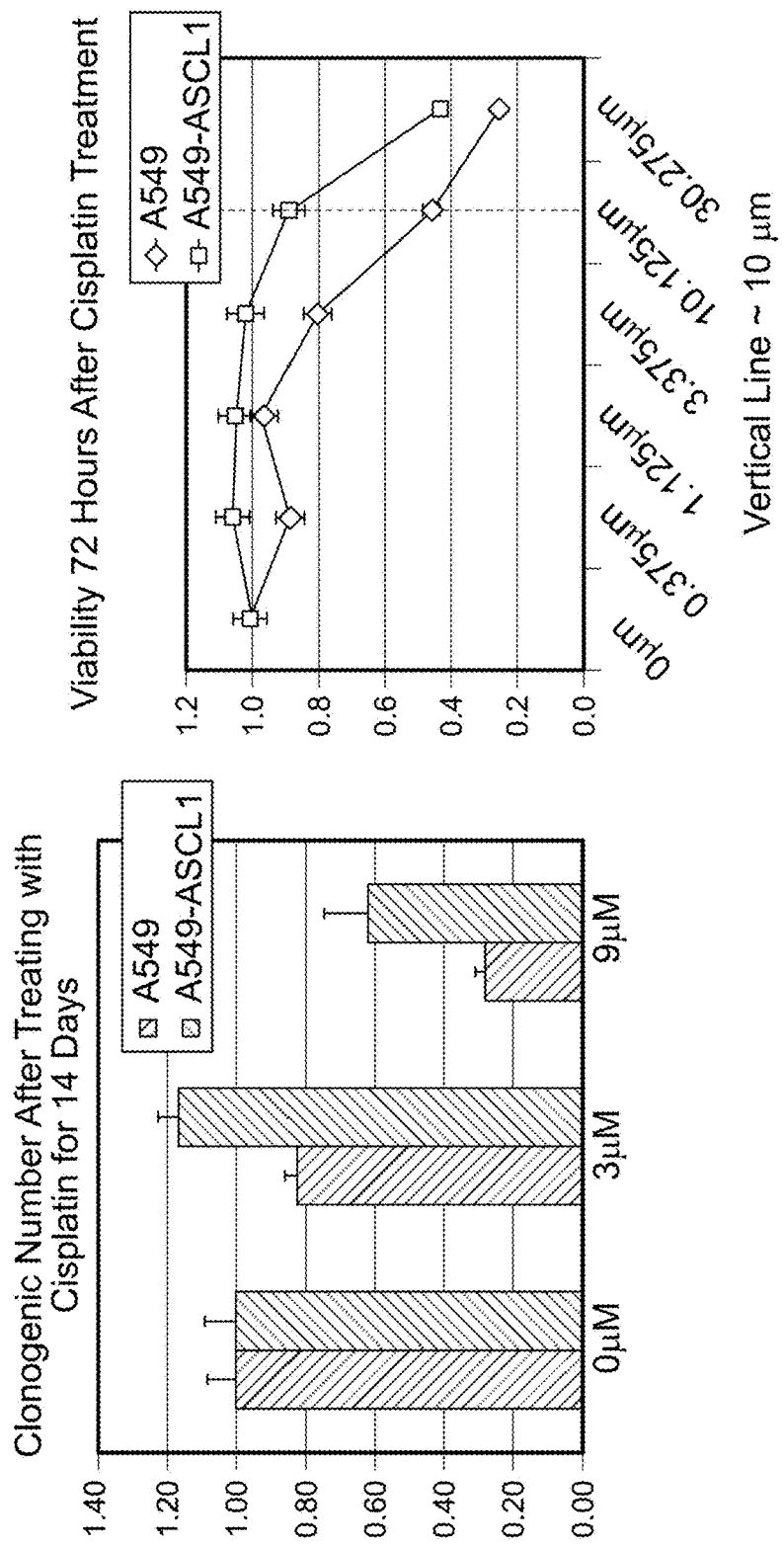
FIG. 15 contains a bar graph plotting the clonogenic number of cells that do not express ASCL1 (A549 cells) and cells that express ASCL1 (A549-ASCL1 cells) after treatment with the indicated amount of cisplatin (e.g., 0 μM, 3
Figure 16:
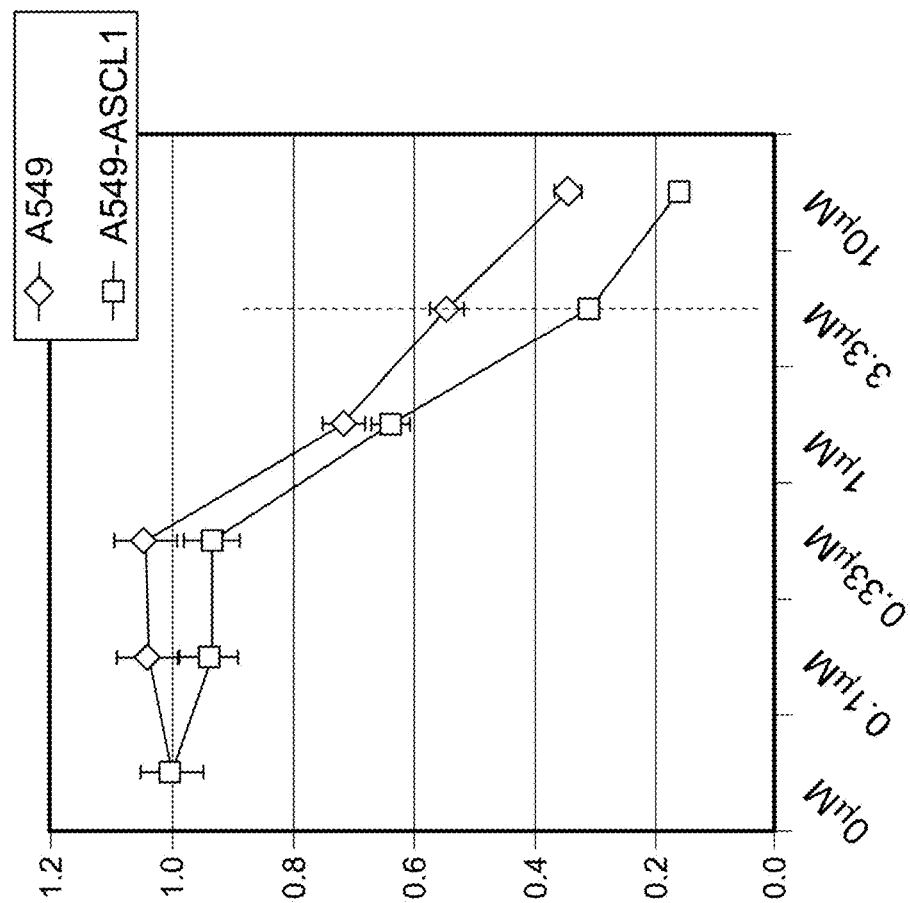
FIG. 16 is a line graph plotting the viability of A549 cells and A549-ASCL1 cells 72 hours after treatment with the indicated amount of sunitinib (marketed as Sutent by Pfizer, and previously known as SU11248). The vertical line is drawn at about 3 μM. These results demonstrate that adenocarcinomas that express ASCL1/RET are more susceptible to treatment by sunitinib.

A549 cells expressed little ASCL1 and RET, while A549 cells transfected with ASCL1 lentivirus (A549-ASCL1 cells or A549-As$^+$ cells) exhibited much more ASCL1 expression (FIG. 13, center). Importantly, A549-As$^+$ cells also expressed high levels of RET, again suggesting that ASCL1 is an up-stream regulator of RET. Also, the A549-As$^+$ cells exhibited increased resistance to cisplatin-induced cytotoxicity (FIG. 15). Furthermore, after cisplatin treatment, the remaining clonogenic potential in ASCL1 over-expressing cells was higher than in cells that did not express ASCL1. The effects of sunitinib, a tyrosine kinase inhibitor, also were examined. A549-As$^+$ cells were more susceptible to sunitinib than the wild type A549 cells (FIG. 16).

Example 4

Treating Lung Adenocarcinoma Characterized by Neuroendocrine Differentiation with Brentuximab Vedotin A patient is identified as having lung adenocarcinoma characterized by neuroendocrine differentiation and is administered Brentuximab vedotin at a dose that is between 1.5 and 2.0 mg/kg (1.8 mg/kg) via intravenous infusion over 30 minutes every 3 weeks.

Example 5

Treating Lung Adenocarcinoma Characterized by Neuroendocrine Differentiation with Sucralfate A patient is identified as having lung adenocarcinoma characterized by neuroendocrine differentiation and is administered sucralfate at a dose of about 1 g (10 mL/2 teaspoonfuls) four times per day.

Example 6

Treating Lung Adenocarcinoma Characterized by Neuroendocrine Differentiation with Paliperidone A patient is identified as having lung adenocarcinoma characterized by neuroendocrine differentiation and is administered paliperidone at a dose of 6 to 12 mg daily orally.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating lung adenocarcinoma, wherein said method comprises:
   (a) detecting the presence of an elevated level of achaete-scute homolog 1 (ASCL1) expression and an elevated level of RET expression in lung adenocarcinoma cells from a mammal, and
   (b) administering a molecule to said mammal under conditions wherein the number of lung adenocarcinoma cells within said mammal is reduced, wherein said molecule is a tyrosine kinase inhibitor.

2. The method of claim 1, wherein said tyrosine kinase inhibitor is a RET inhibitor.

3. The method of claim 1, wherein said tyrosine kinase inhibitor is sunitinib.

4. The method of claim 1, wherein said tyrosine kinase inhibitor is vandetanib.

5. The method of claim 1, wherein said mammal is a human.

6. A method for treating lung adenocarcinoma, wherein said method comprises administering a molecule to a mammal identified as having lung adenocarcinoma cells comprising an elevated level of achaete-scute homolog 1 (ASCL1) expression and an elevated level of RET expression under conditions wherein the number of lung adenocarcinoma cells within said mammal is reduced, wherein said molecule is a tyrosine kinase inhibitor.

7. The method of claim 6, wherein said mammal is a human.

8. The method of claim 6, wherein said tyrosine kinase inhibitor is a RET inhibitor.

9. The method of claim 6, wherein said tyrosine kinase inhibitor is sunitinib.

10. The method of claim 6, wherein said tyrosine kinase inhibitor is vandetanib.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 1
gccaacaaga agatgagtaa g                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 2
caaccgcgtc aagttggtca a                                              21
```